(12) United States Patent  
Wawrzyniak et al.

(10) Patent No.: US 8,852,119 B2
(45) Date of Patent: Oct. 7, 2014

(54) BONE MARROW HARVESTING DEVICE HAVING FLEXIBLE NEEDLE

(75) Inventors: Kortney Wawrzyniak, West Chester, PA (US); Peter Kurzyna, West Chester, PA (US); Michael Lehmicke, West Chester, PA (US); Sean Kerr, West Chester, PA (US); John Maurice Marthaler, Santa Rosa, CA (US); Steven Paul Parmelee, Santa Rosa, CA (US)

(73) Assignee: DePuy Synthes Products, LLC, Raynham, MA (US)

( * ) Notice: Subject to any disclaimer, the term of this patent is extended or adjusted under 35 U.S.C. 154(b) by 420 days.

(21) Appl. No.: 13/253,461

(22) Filed: Oct. 5, 2011

(65) Prior Publication Data

US 2012/0116247 A1    May 10, 2012

Related U.S. Application Data

(60) Provisional application No. 61/389,889, filed on Oct. 5, 2010.

(51) Int. Cl.
*A61B 10/00*    (2006.01)
*A61B 10/02*    (2006.01)

(52) U.S. Cl.
CPC ....... *A61B 10/025* (2013.01); *A61B 2010/0258* (2013.01)
USPC .......................................... 600/566; 604/272

(58) Field of Classification Search
CPC ............. A61B 17/8811; A61B 10/025; A61B 2010/0258
USPC ................................... 600/566, 567; 604/272
See application file for complete search history.

(56) References Cited

U.S. PATENT DOCUMENTS

| | | | |
|---|---|---|---|
| 2,515,365 | A | 7/1950 | Zublin et al. |
| 4,142,517 | A | 3/1979 | Stavropoulos et al. |
| 4,469,109 | A | 9/1984 | Mehl |
| 5,707,350 | A | 1/1998 | Krause et al. |
| 6,053,922 | A * | 4/2000 | Krause et al. .................. 606/80 |
| 6,447,518 | B1 | 9/2002 | Krause et al. |
| 6,890,308 | B2 | 5/2005 | Islam |
| 6,916,292 | B2 | 7/2005 | Morawski et al. |
| 7,081,123 | B2 | 7/2006 | Merboth et al. |
| 7,229,439 | B2 | 6/2007 | Burbank et al. |
| 7,625,364 | B2 | 12/2009 | Corcoran et al. |
| 2004/0054377 | A1 | 3/2004 | Foster et al. |
| 2005/0177168 | A1* | 8/2005 | Brunnett et al. ............... 606/80 |
| 2006/0173244 | A1* | 8/2006 | Boulais et al. ............... 600/156 |
| 2007/0197996 | A1 | 8/2007 | Kraft et al. |
| 2007/0276352 | A1 | 11/2007 | Crocker et al. |
| 2009/0054807 | A1 | 2/2009 | Taylor et al. |

(Continued)

FOREIGN PATENT DOCUMENTS

GB        2130890        6/1984

*Primary Examiner* — Max Hindenburg
*Assistant Examiner* — Renee Danega
(74) *Attorney, Agent, or Firm* — Wayne C. Jaeschke, Jr.

(57) ABSTRACT

A bone marrow harvesting device includes a flexible bone marrow harvesting needle that can bend during operation to prevent the needle tip from piercing the inner cortical wall of the target bone. The needle defines an aspiration channel that defines an intake end that is recessed to reduce the instances that the aspiration channel will be fouled by bone particles or other debris within the cancellous portion.

25 Claims, 14 Drawing Sheets

(56) References Cited

U.S. PATENT DOCUMENTS

| | | |
|---|---|---|
| 2009/0131886 A1* | 5/2009 | Liu et al. .................. 604/272 |
| 2009/0187116 A1 | 7/2009 | Noishiki et al. |
| 2010/0030105 A1 | 2/2010 | Noishiki et al. |
| 2010/0305595 A1 | 12/2010 | Hermann |
| 2011/0004215 A1 | 1/2011 | Bradley et al. |

* cited by examiner

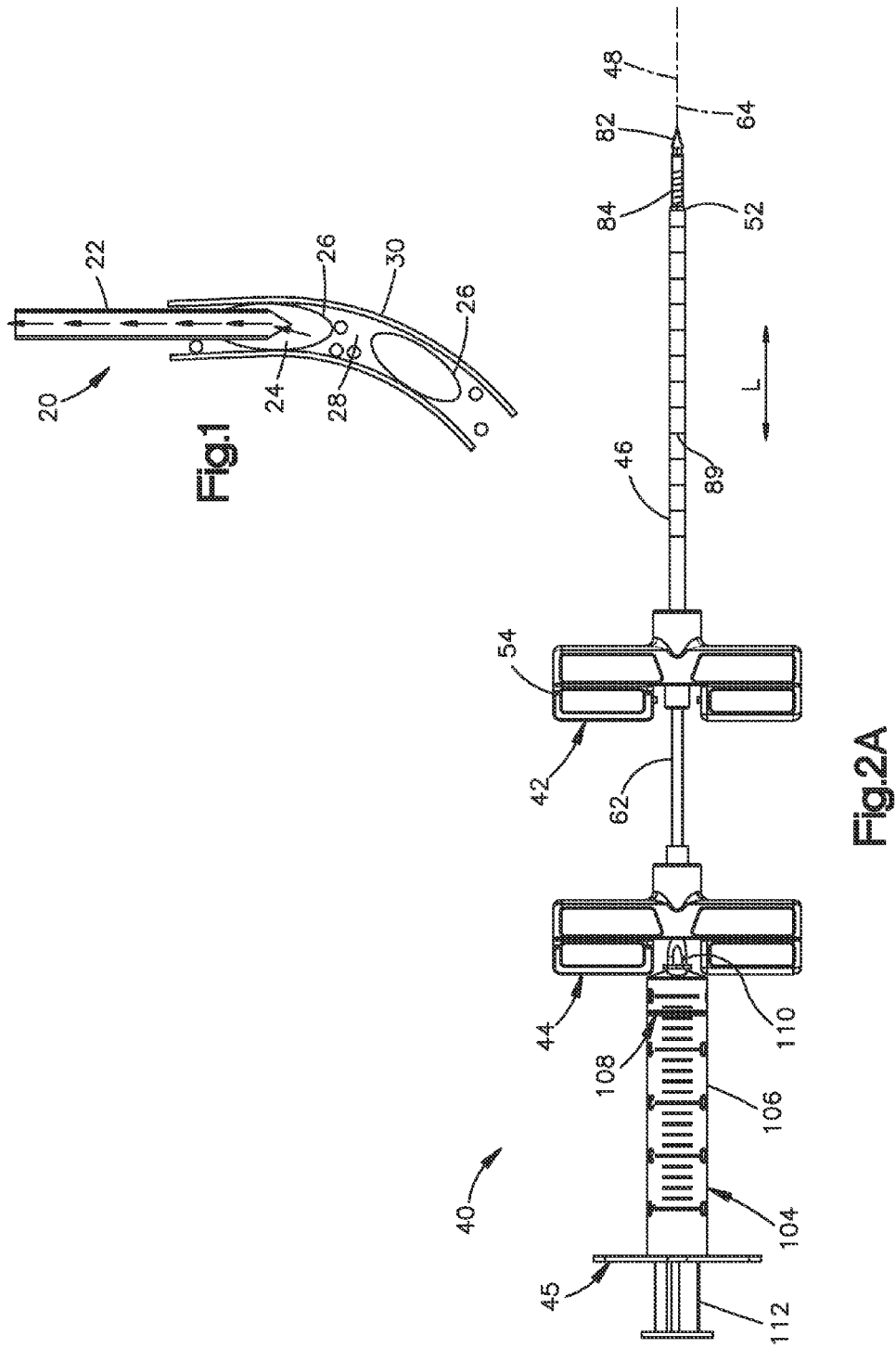

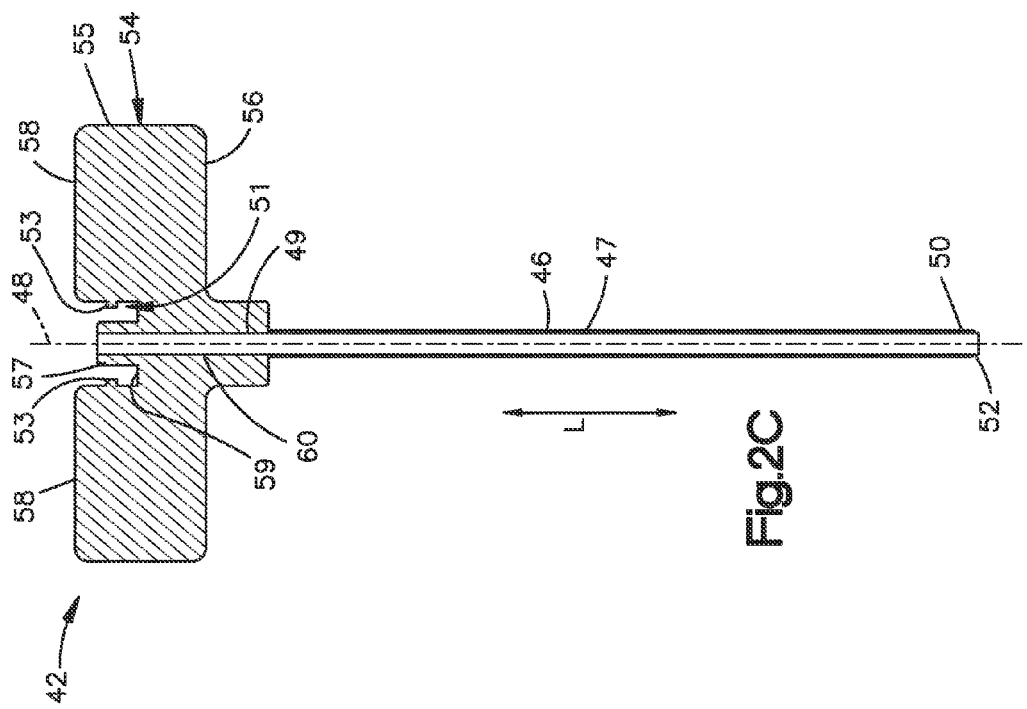
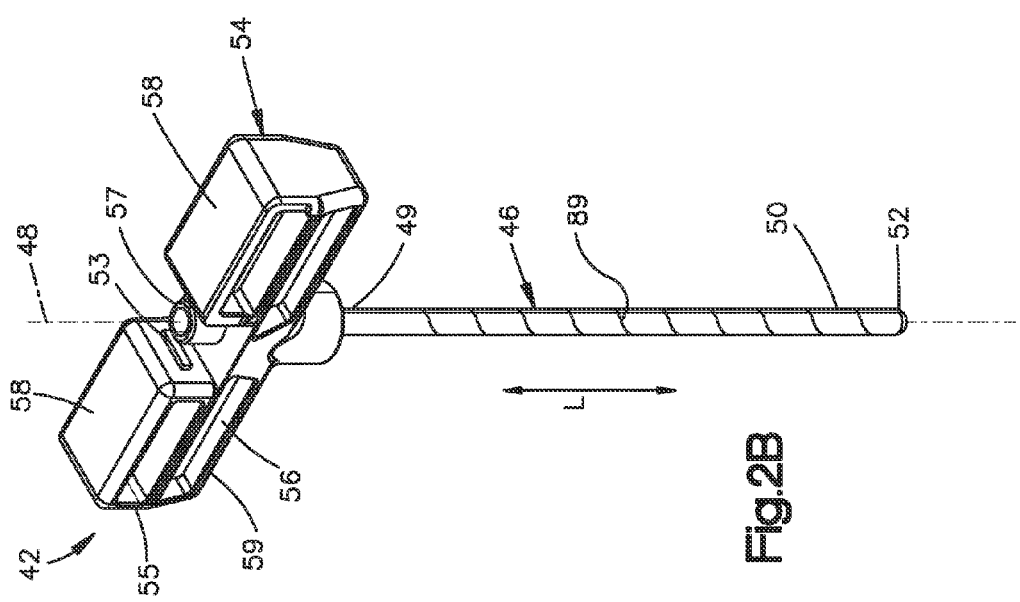

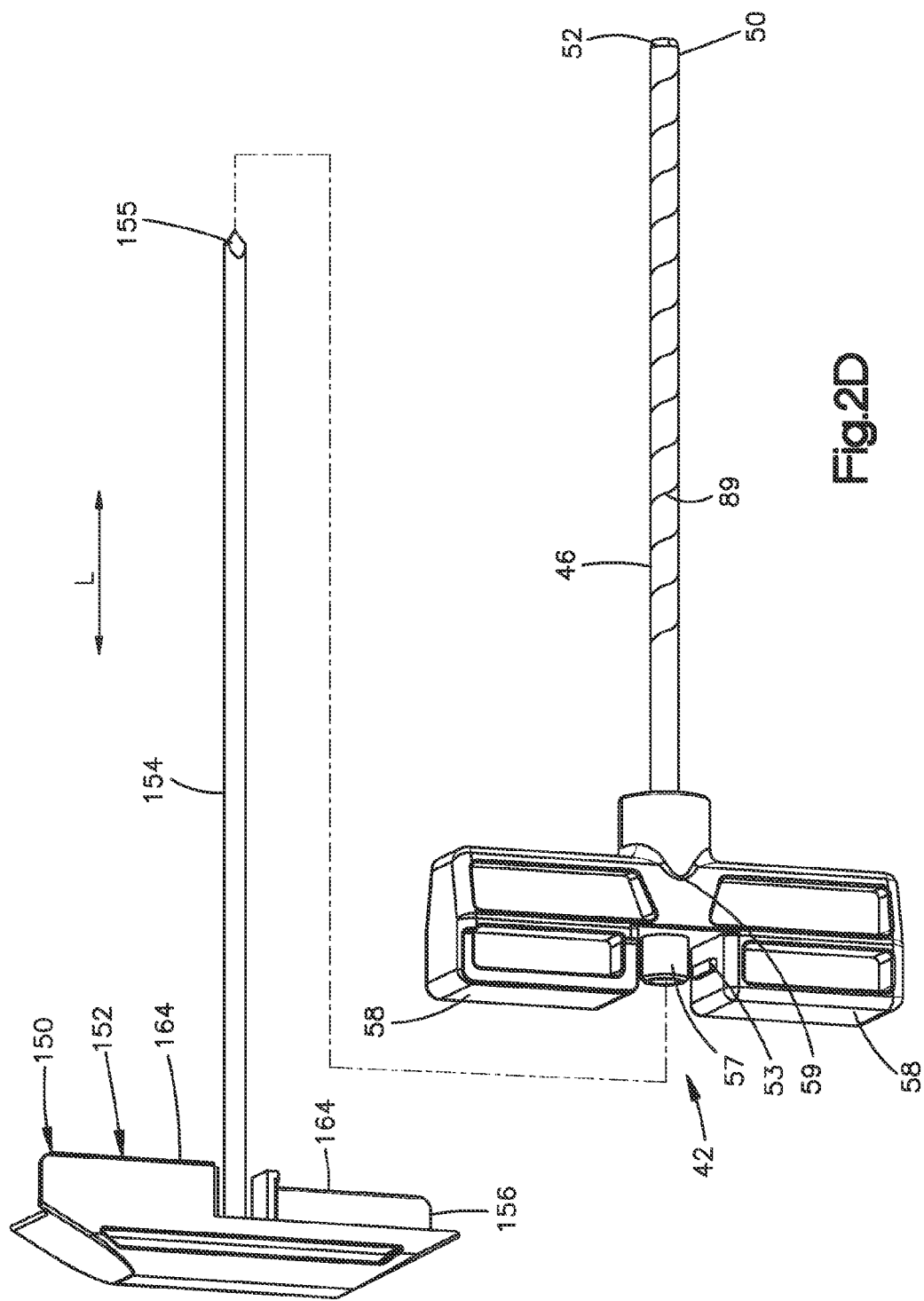

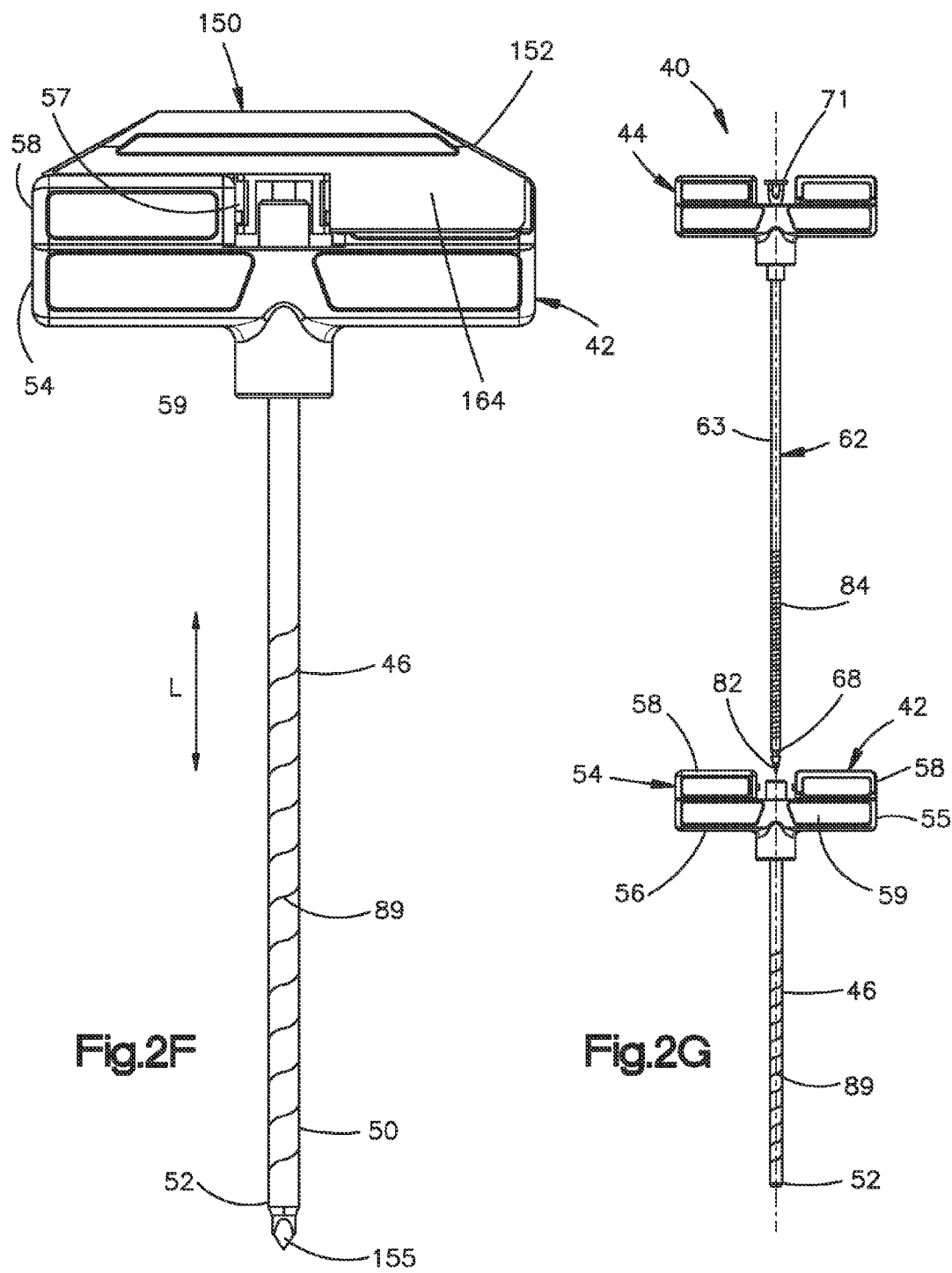

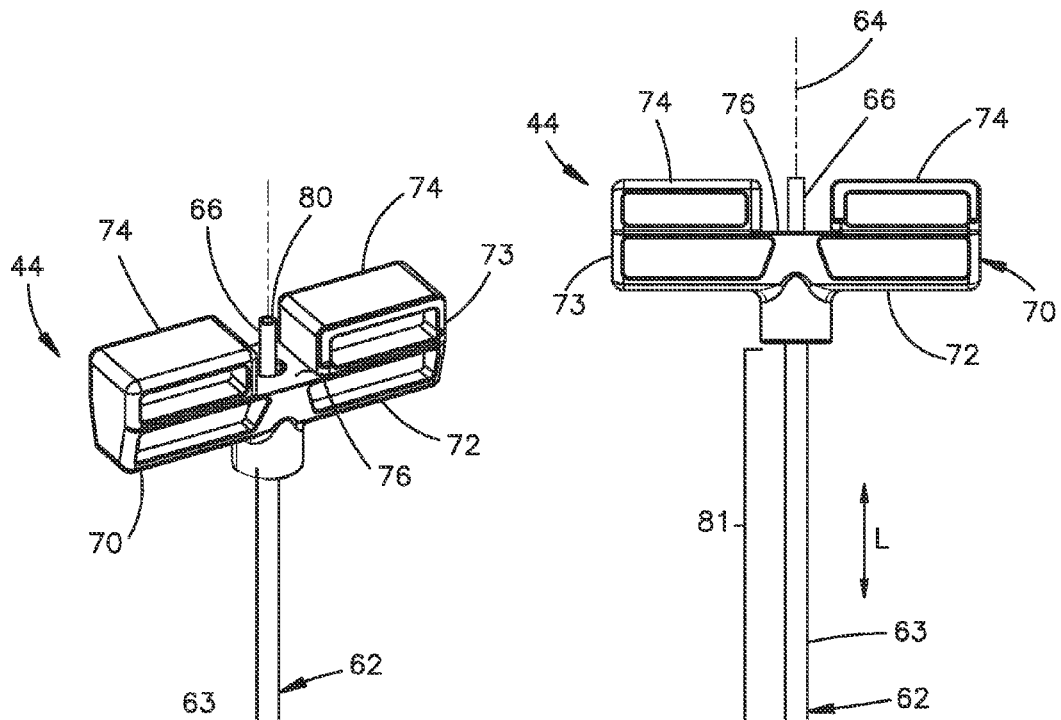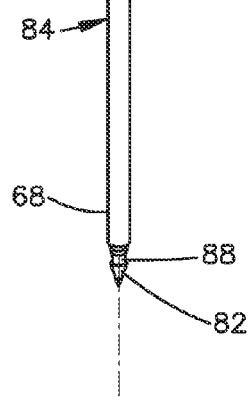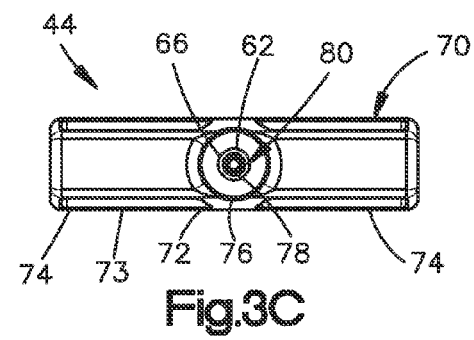

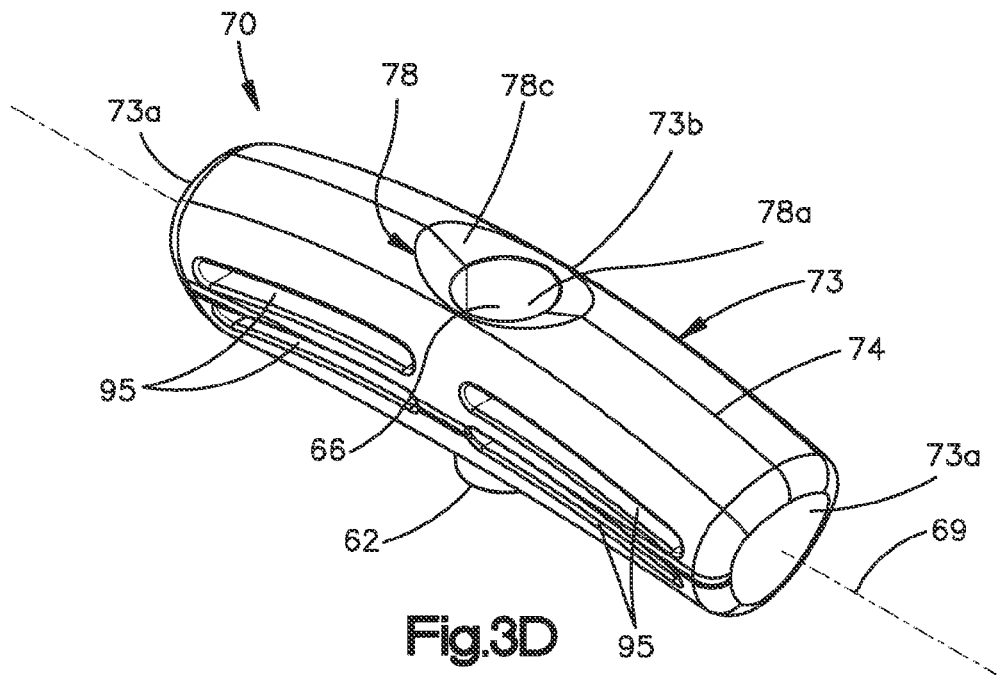
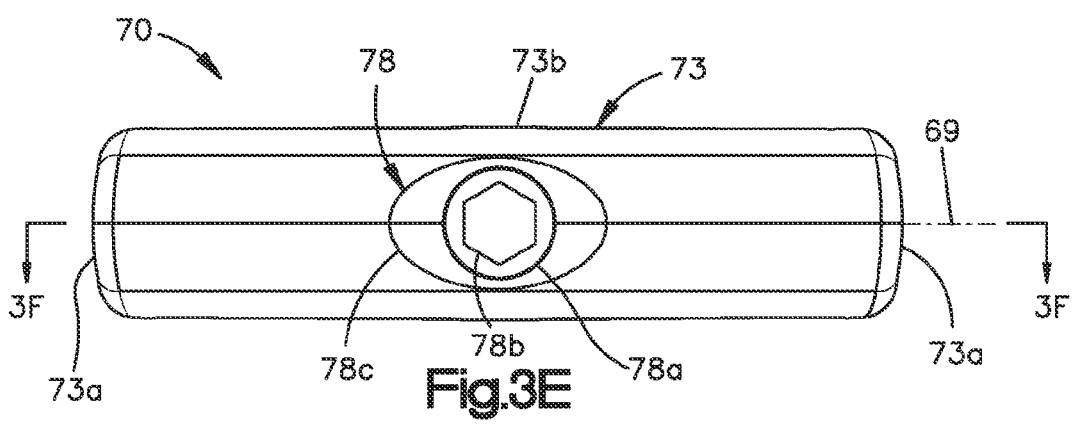
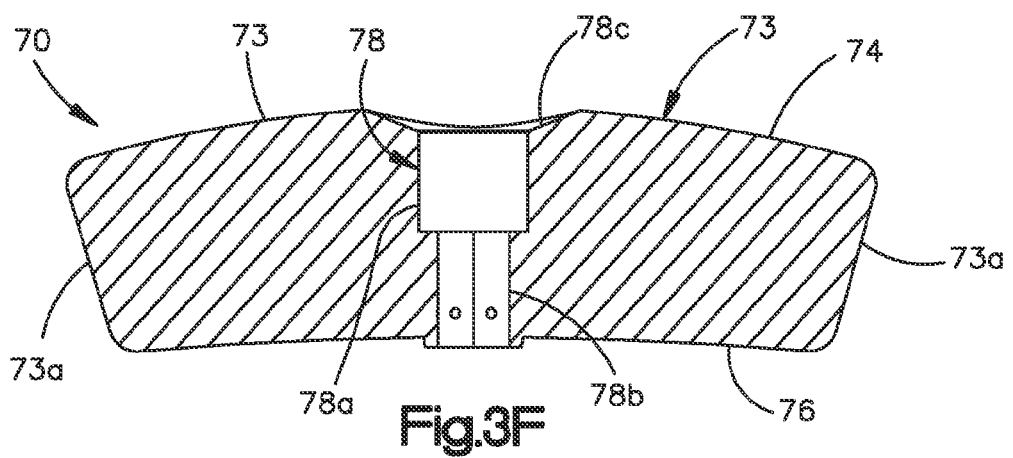

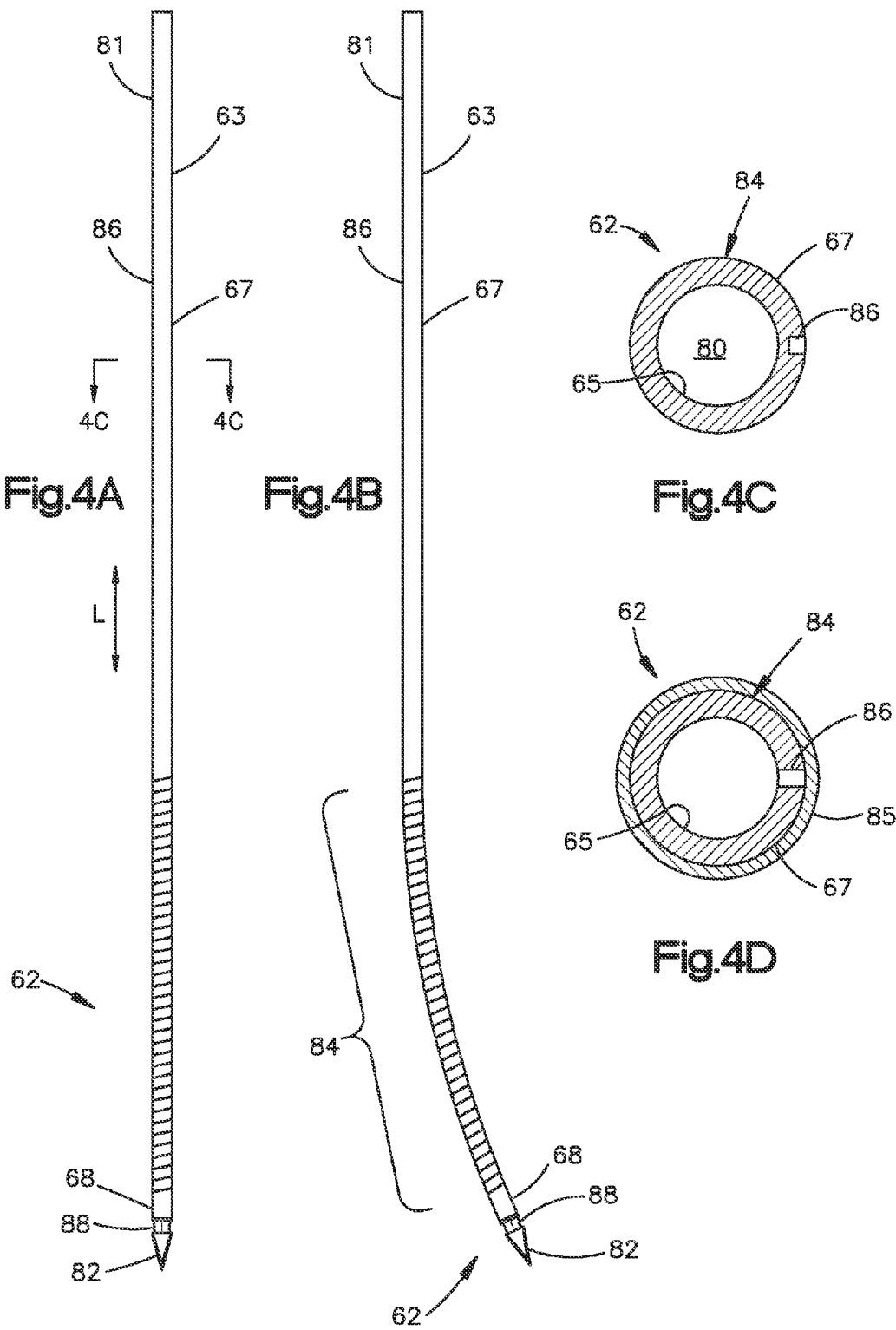

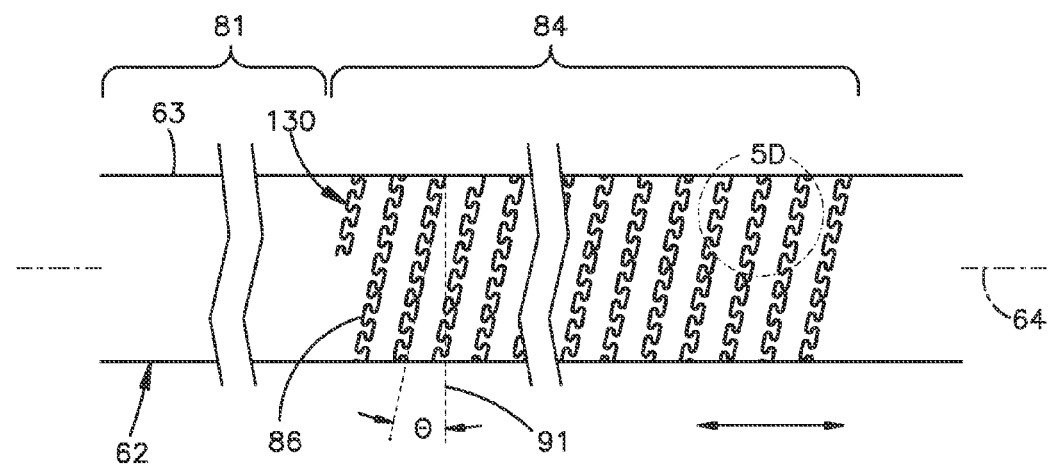
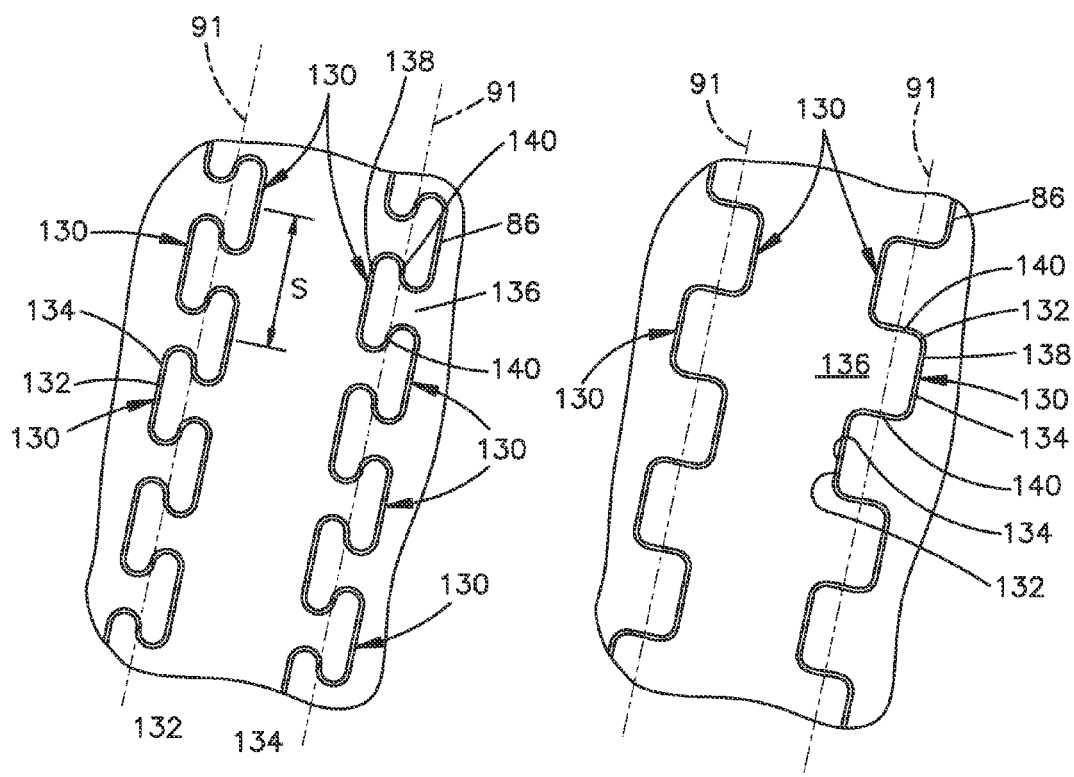
Fig.5C
Fig.5D    Fig.5E

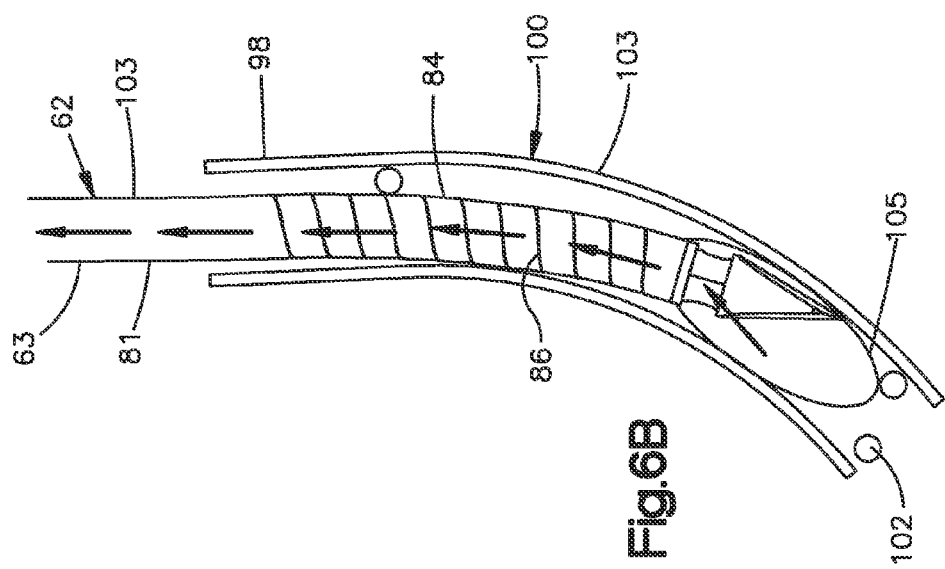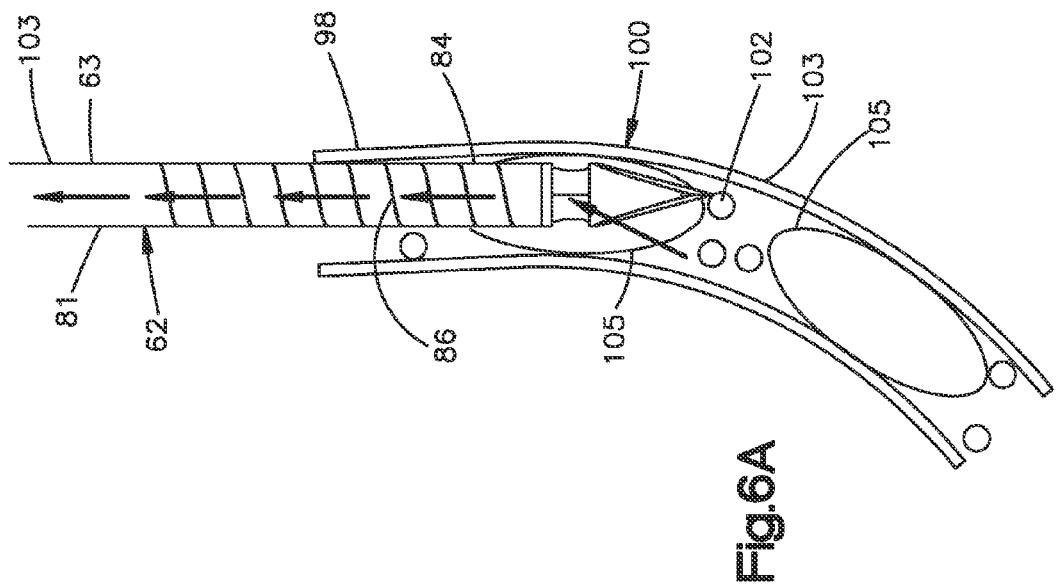

BONE MARROW HARVESTING DEVICE HAVING FLEXIBLE NEEDLE

CROSS-REFERENCE TO RELATED APPLICATIONS

This claims the benefit of U.S. Patent Application Ser. No. 61/389,889, filed Oct. 5, 2010, the disclosure of which is hereby incorporated by reference as if set forth in its entirety herein.

BACKGROUND

Referring to FIG. 1, conventional bone marrow harvesting devices typically include a straight and rigid Jamshidi needle 20, which typically defines an elongate hollow tube 22 having a cutting tip 24 at a distal end, a handle at an opposed proximal end (not shown), and a syringe or other suitable receptacle that is in fluid communication with the tube 22. During operation, a trocar is typically driven through the hard cortex of a target bone 30, and the needle 20 is then inserted through a cannulation of the trocar and into the cancellous portion 28 of the bone 30. A negative pressure is induced in the needle 20 to aspirate bone marrow 26 from the cancellous portion 28 of the target bone 30 through the needle 20 and into the receptacle.

It has been found that rigid bone marrow harvesting needles stand the risk of inadvertently puncturing the cortical wall of the target bone during advancement through the cancellous portion of the target bone, particularly when the bone marrow harvesting needle is being driven along the cancellous portion of a curved region of the target bone. What is desired is a bone marrow harvesting device that is configured to aspirate bone marrow from a target bone more reliably than conventional bone marrow harvesting devices.

SUMMARY

In accordance with one embodiment, a bone marrow harvesting device comprises a bone marrow needle that includes a needle shaft that is elongate along a central axis. The needle shaft includes a shaft body that defines an aspiration channel that extends through the central axis. The needle shaft further defines an intake port in fluid communication with the aspiration channel so as to draw bone marrow aspirate from a target bone. The shaft body includes a flexible portion defining a single continuous groove that extends into the shaft body. The single continuous groove extends along a substantially helical path along a length of the shaft body. The bone marrow needle further includes a tip that extends distally from the needle shaft, and a non-elastomeric overcoat that extends over the flexible portion and covers at least a portion of the groove. The bone marrow harvesting device further includes a trocar including a trocar handle and a cannulated shaft that extends from the trocar handle, the cannulated shaft configured to slidingly receive at least a portion of the needle shaft, and a receptacle configured to be operatively coupled to the needle so as to aspirate bone marrow from a target bone through the needle and collect the aspirated bone marrow.

BRIEF DESCRIPTION OF THE DRAWINGS

The foregoing summary, as well as the following detailed description of a preferred embodiment, are better understood when read in conjunction with the appended diagrammatic drawings. For the purpose of illustrating the present disclosure, reference to the drawings is made. The scope of the disclosure is not limited, however, to the specific instrumentalities disclosed in the drawings. In the drawings:

FIG. 1 is a schematic side elevation view of a conventional bone marrow harvester needle;

FIG. 2A is a schematic side elevation view of a bone marrow harvesting device constructed in accordance with one embodiment, including a trocar, a bone marrow harvesting needle configured to aspirate bone marrow from a target bone, and a receptacle configured to receive the aspirated bone marrow;

FIG. 2B is a perspective view of the trocar illustrated in FIG. 2A;

FIG. 2C is a sectional side elevation view of the trocar illustrated in FIG. 2A;

FIG. 2D is an exploded perspective view of the trocar illustrated in FIG. 2A and a stylet configured to be inserted through the trocar so as to be driven through the cortex of the target bone;

FIG. 2F is a side elevation view of the stylet illustrated in FIG. 2D shown inserted through the trocar;

FIG. 2G is an exploded assembly view of the needle and the trocar illustrated in FIG. 2A;

FIG. 3A is a perspective view of the bone marrow harvesting needle illustrated in FIG. 2A;

FIG. 3B is a side elevation view of the bone marrow harvesting needle illustrated in FIG. 3A;

FIG. 3C is an end elevation view of the bone marrow harvesting needle illustrated in FIG. 3B;

FIG. 3D is a perspective view of a needle handle in accordance with an alternative embodiment, shown connected to a needle shaft of the bone marrow harvesting needle illustrated in FIG. 3A;

FIG. 3E is a top plan view of the needle handle illustrated in FIG. 3D;

FIG. 3F is a sectional side elevation view taken along line 3F-3F of FIG. 3E;

FIG. 4A is a side elevation view of a flexible shaft portion of the bone marrow harvesting needle illustrated in FIG. 2A in a straight configuration;

FIG. 4B is a side elevation view of the flexible shaft portion of the bone marrow harvesting needle illustrated in FIG. 4A, shown in a flexed configuration;

FIG. 4C is a sectional end elevation view of the bone marrow harvesting needle illustrated in FIG. 4B, taken along line 4C-4C;

FIG. 4D is a sectional end elevation view similar to FIG. 4C, but constructed in accordance with an alternative embodiment;

FIG. 5C is a schematic side elevation view of the flexible shaft portion similar to FIG. 4A, but constructed in accordance with an alternative embodiment;

FIG. 5D is an enlarged side elevation view of a portion of the flexible shaft portion illustrated in FIG. 5C, taken along line 5D;

FIG. 5E is an enlarged side elevation view of a portion of the flexible shaft portion similar to FIG. 5D, but including a groove constructed in accordance with an alternative embodiment;

FIG. 6A is a schematic elevation view of the bone marrow harvesting needle inserted into the cancellous portion of a target bone in a straight configuration;

FIG. 6B is a schematic elevation view of the bone marrow harvesting needle inserted into the cancellous portion of a target bone similar to FIG. 6A, but showing the needle in a flexed configuration;

DETAILED DESCRIPTION

Figure 2E:
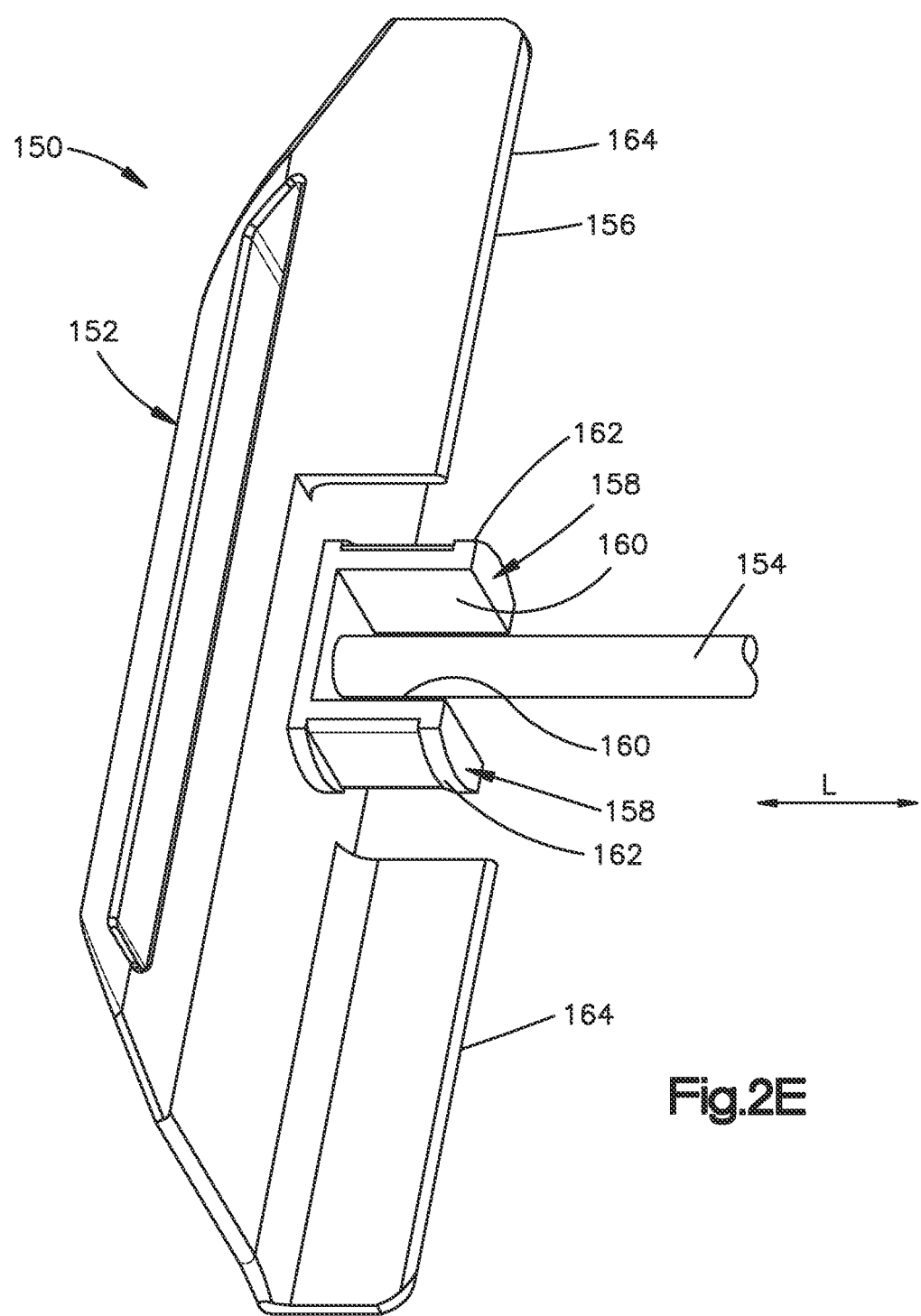
FIG. 2E is a side elevation view of a proximal end of the stylet illustrated in FIG. 2D.
Figure 2H:
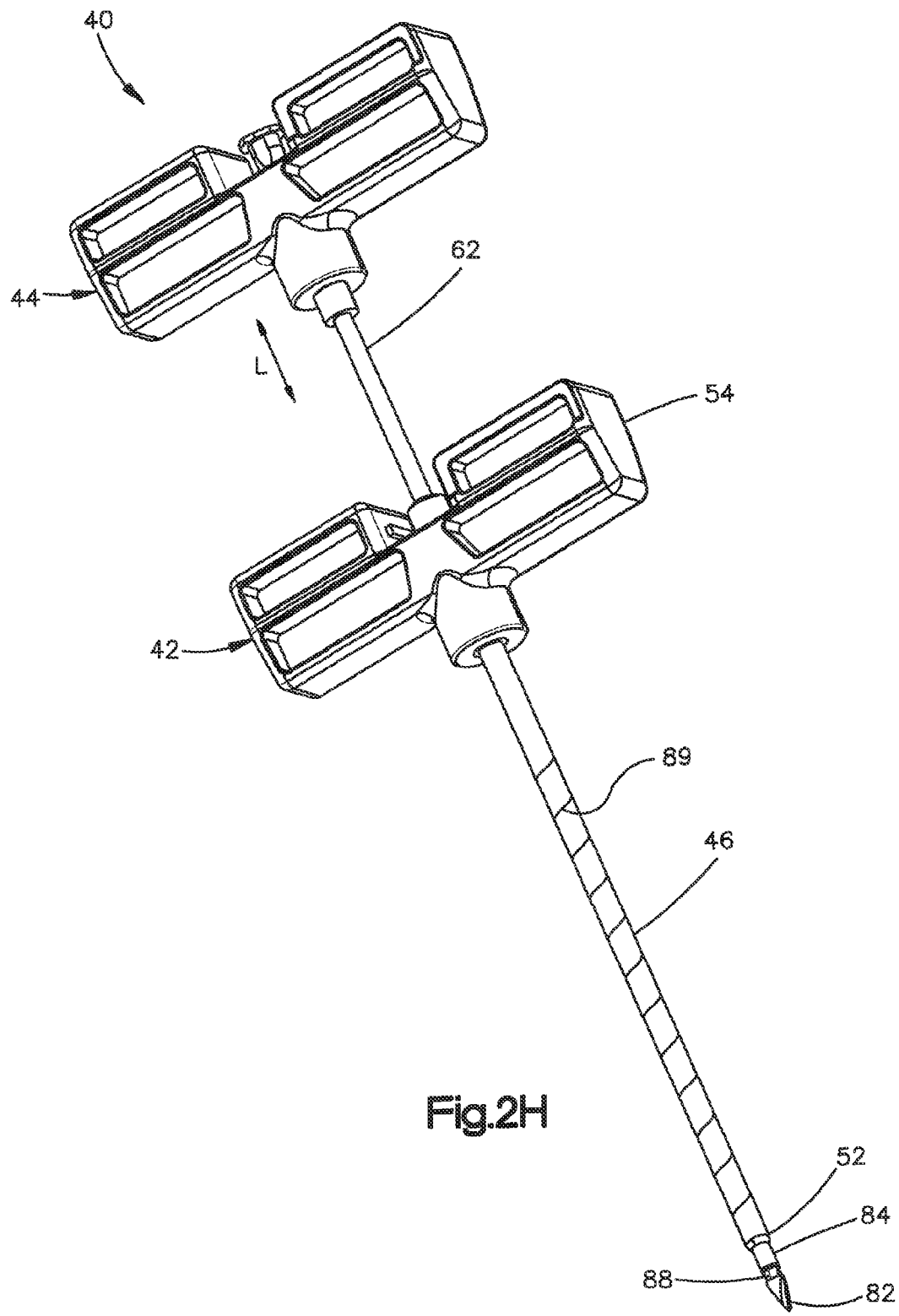
FIG. 2H is a perspective view of the needle inserted through the trocar illustrated in FIG. 2G.

Referring to FIG. 2A-C, a bone marrow harvesting device 40 includes a cannulated trocar 42, a cannulated bone marrow harvesting needle 44 configured to be inserted through the trocar 42 and into a target bone so as to aspirate bone marrow from the target bone, and a receptacle 45 configured to be operatively coupled to the needle 44 so as to receive and collect the aspirated bone marrow. The target bone can be any bone that contains a suitable amount of bone marrow to be harvested. In accordance with one embodiment, the target bone can be the pelvis. As will be appreciated from the description below, at least a portion of the needle 44 is flexible, thereby allowing the bone marrow harvesting device 40 to more reliably aspirate bone marrow from the target bone as opposed to conventional bone marrow harvesting devices that have rigid needles.

The trocar 42 includes a cannulated trocar shaft 46 that defines a proximal end 49 and a distal end 50 that is opposite the proximal end 49 along a central trocar shaft axis 48 that can extend substantially along a longitudinal direction L. It should thus be appreciated that the terms "proximal," "distal," and derivatives thereof as used with respect to the trocar 42 and components thereof are made with reference to a direction from the distal end 50 toward the proximal end 49, and a direction from the proximal end 49 toward the distal end 50, respectively. The trocar shaft 46 defines a trocar tip 52 at the distal end 50.

The trocar 42 includes a trocar handle 54 coupled to the proximal end 49 of the trocar shaft 46, such that the trocar shaft 46 extends distally from the trocar handle 54. The trocar handle 54 can be made from any polymer or any suitable alternative material, and the trocar shaft 46 can be made from stainless steel, titanium or any suitable alternative material, such as a biocompatible material or a shape-memory material such as nitinol. In accordance with the embodiment illustrated in FIG. 2A-D, the trocar handle 54 includes a trocar handle body 55 that can include a plate 56 and at least one grip member 58, such as a pair of grip members 58 that extend out, for instance proximally, from the plate 56. The grip members 58 can be spaced such that the trocar handle body 55 defines a bridge portion 59 connected between the grip members 58. The trocar handle body 55 further includes a cannulated connector 57 that extends proximally from the bridge portion 59 at a location aligned with the cannulated shaft 46. The plate 56 defines an aperture 60 that extends longitudinally through the trocar handle body 55, for instance through the bridge portion 59 and the connector 57. At least a portion of the aperture 60 is sized to retain the proximal end 49 of the trocar shaft 46. The plate 56 can be discreetly connected to the trocar shaft 46 or can be integral with the trocar shaft 46. In accordance with the illustrated embodiment, the trocar handle 54 is overmolded onto the proximal end 49 of the trocar shaft 46.

The trocar shaft 46 can be cannulated, such that the trocar 42 defines a cannulation 47 that extends through the trocar shaft 46 along the central axis 48 from the proximal end 49 to the distal end 50, such that the cannulation 47 is in alignment with the aperture 60 along the central axis 48. In accordance with the illustrated embodiment, the proximal end 49 terminates in the trocar handle body 55, for instance in the bridge portion 59, though it should be appreciated that the proximal end 49 alternatively extend proximally out from the trocar handle 54.

Referring now to FIGS. 2D-F, the bone marrow harvesting device 40 can further include a stylet 150 that is configured to be inserted through the trocar shaft 46 so as to be driven through the cortex of a target bone (via a punching or drilling motion, or any suitable alternative motion). The stylet 150 includes a stylet handle 152, a stylet shaft 154 that extends distally from the stylet handle 152, and a stylet tip 155 that extends distally from the stylet shaft 154.

The stylet handle 152 includes a handle body 156 and at least one engagement member such as a pair of engagement members 158 that extend from the handle body 156. In accordance with the illustrated embodiment, the engagement members 158 are configured as flexible tabs 160 that extend distally from the handle body 156, and are spaced apart a distance sufficient so as to receive the connector 57 of the trocar handle 54 when the stylet 150 is coupled to the trocar 42. Each of the engagement members 158 can further include a lip 162 that projects out from the distal end of the respective flexible tab 160.

The engagement members 158 of the stylet 150 are configured to mate with complementary engagement members 51 of the trocar handle 54 (see also FIGS. 2B-C) so as to attach the stylet 150 to the trocar 42. For instance the engagement members 51 of the trocar handle 54 can be configured as at least one protrusion such as a pair of protrusions 53 that project inwardly, and thus toward each other, from respective inner surfaces of the grip members 58. The protrusions 53 are spaced proximally with respect to the bridge portion 59, and terminate at a location outwardly spaced with respect to the connector 57. Thus, the trocar handle 54 defines respective first gaps disposed between a proximal surface of the bridge portion 59 and respective distal surfaces of the protrusions 53 when the stylet 150 is removably attached to the trocar 42. The first gap is sized to receive a corresponding one of the lips 162. The trocar handle 54 further defines respective second gaps disposed between the protrusions 53 and the connector 57. The second gaps are sized to receive the tabs 160 of the stylet 150 when the stylet 150 is attached to the trocar 42.

The stylet shaft 154 defines an outer diameter (or alternatively shaped cross-sectional dimension) that is substantially equal to or slightly less than that of the cannulation 47 of the trocar shaft 46, such that the stylet shaft 154 can be received in the cannulation 47 so that the stylet shaft 154 can translate within the cannulation 47 along the longitudinal direction L. The stylet shaft 154 has a length along the longitudinal direction L that is sized such that the stylet tip 155 projects distally with respect to the trocar shaft 46 when the stylet 150 is attached to the trocar 42. The stylet tip 155 can be tapered as it extends distally in accordance with the illustrated embodiment.

During operation, the stylet shaft 154 is initially inserted through the aperture 60 of the trocar handle 54 and further through the cannulation 47 of the trocar shaft 46 until the stylet handle 152 is seated against the trocar handle 54. In accordance with the illustrated embodiment, the stylet handle 152 is seated against the trocar handle 54 when the distal surface of the stylet handle body 156 abuts the proximal surface of the trocar handle 54, which can be the proximal surface of the connector 57. The stylet shaft 154 can be initially inserted into the trocar shaft 56 when the stylet handle 152 is oriented substantially perpendicular to the trocar handle 54. Accordingly, the engagement member of the stylet handle 152 is free from interference with the engagement member of the trocar handle 54. In particular, the tabs 160 of the stylet handle 152 are radially offset with respect to the projections 53 of the trocar handle 54 when the stylet shaft 154 is initially inserted through the trocar shaft 46.

Once the stylet handle 152 is seated against the trocar handle 54, the one or both of the stylet handle 152 and the trocar handle 54 can be rotated relative to the other until the flexible tabs 160 of the stylet handle 152 bear against the protrusions 53 of the trocar handle 54 in the second gap of the trocar handle 54. In particular the inner surfaces of the protrusions 53 of the trocar handle 54 can be spaced apart a first distance, and the outer surfaces of the tabs 60 can be spaced apart a second distance that is slightly greater than the first distance. Accordingly, the protrusions 53 bias the tabs 60 to flex inwardly toward each other so as to provide a frictional force between the tabs 60 and the protrusions 53 that releasably attaches the stylet handle 152 to the trocar handle 54. The lips 162 are disposed in the first gap of the trocar handle 54 between the respective protrusions 53 and the bridge portion 59. The stylet handle 152 can further include a pair of opposed abutment surfaces 164 that can abut the trocar handle 54 when the stylet handle 152 has been rotated sufficiently so as to mate the engagement members 158 of the stylet 150 with the complementary engagement members 51 of the trocar 42. It should be appreciated that at least one of the stylet handle 152 and the trocar handle 54 can be rotated in an opposite direction so as to disengage the engagement members 158 and 51, such that the stylet 150 can be removed from the trocar 42.

When the stylet 150 is attached to the trocar 42, the stylet tip 155 projects distally with respect to the tip 52 of the trocar shaft 46. Accordingly, the stylet tip 155 can be placed against the cortex of the target bone, and a driving force, for instance a repeated tapping force of a mallet, can be applied to the stylet handle 150, which causes the stylet tip 155, and thus also the trocar shaft 46, to drive into and through the cortex of the target bone. It should be appreciated that the driving force can be any suitable driving force as desired, such as a tapping force, a punching force, a drilling force, or any alternative force suitable to drive the stylet tip 155 and the trocar shaft through the cortical wall of the target bone. The trocar shaft 46 can include depth markings 89 that indicate the depth to which the trocar shaft 46 has been inserted into the target bone. For instance, it can be desired to insert the trocar shaft 46 into the target bone at a depth sufficient to ensure that the trocar tip 52 is disposed in the cancellous portion of the target bone. Once the stylet tip 155 has been driven through the cortical wall of the target bone, the stylet 150 can be removed from the trocar 42, such that the cannulation 47 of the trocar shaft 46 provides a guide path for the needle 44 to be advanced relative to the trocar 44 and into the cancellous portion of the target bone.

While the stylet 150 and the trocar 42 have been described in accordance with one embodiment, it should be appreciated that the bone marrow harvesting device 40 can be constructed in accordance with any suitable alternative embodiment. For instance, the engagement members 158 of the stylet 150 and the engagement members 51 of the trocar 42 can be alternatively configured as desired so as to releasably attach the stylet 150 to the trocar 42. Alternatively still, the stylet 150 and the trocar 42 can be devoid of complementary engagement members, such that the driving force can be applied to the stylet handle 152 when the stylet handle 152 is in mechanical communication with the trocar handle 54. Alternatively still, the stylet tip 155 can be driven through the cortical wall of the target bone, thereby defining an opening that extends through the cortical wall, without first inserting the stylet 150 through the trocar 42. In this alternative embodiment, the stylet 150 can be removed from the target bone after having been driven through the cortical wall, and the distal end 50 of the trocar shaft 46 can subsequently be inserted through the cortical wall opening created by the stylet 150. Alternatively still, the bone marrow harvesting device 40 can be devoid of the stylet 150, and the trocar tip 52 can be configured to be driven through the cortical wall of the target bone, such that the cannulation 47 of the trocar shaft 46 defines the guide path for the needle 44 to be advanced relative to the trocar 44 and into the cancellous portion of the target bone.

Referring now to FIGS. 2G-3C, the needle 44 includes a cannulated needle shaft 62 that defines a proximal end 66 and a distal end 68 that is opposite the proximal end 66 along a central needle shaft axis 64. It should thus be appreciated that the terms "proximal," "distal," and derivatives thereof as used with respect to the needle 44 and components thereof are made with reference to a direction from the distal end 68 toward the proximal end 66, and a direction from the proximal end 66 toward the distal end 68, respectively. The needle shaft 62 can define any length as desired between the proximal and distal ends 66 and 68, for instance between approximately 7.5 inches and approximately 12 inches, including approximately 9.5 inches in accordance with one embodiment, and approximately 11 inches in accordance with another embodiment.

The central axis 64 can extend along the longitudinal direction L when the needle shaft 62 is in an unflexed, or straight, configuration. The needle shaft 62 can include a flexible needle shaft body 63 that can define a first body portion such as a rigid portion 81 that can be substantially rigid, and a second body portion such as a flexible portion 84 that can extend distally from the rigid portion 81. The needle shaft body 63 can extend substantially along the longitudinal direction L when the flexible body portion 84 is in a first unflexed configuration. As described in more detail below, the flexible portion 84, and thus the shaft body 63, is configured to iterate from the first unflexed configuration to a second flexed configuration whereby the central axis 64 defined by at least some up to substantially all of the flexible portion 84 is angularly offset with respect to the longitudinal direction L.

With continuing reference to FIGS. 2G-3C, the needle 44 includes a needle handle 70 coupled to the proximal end 66 of the needle shaft 62. The needle 44 and the needle handle 70 can be made from any material as desired, such as stainless steel, titanium, aluminum, polymer, or the like, and can be biocompatible as desired. The needle handle 70 can be constructed in accordance with any suitable embodiment as desired. For instance, in accordance with one embodiment, the handle 70 includes a needle handle body 73 that can include a plate 72 and at least one grip member 74 such as a pair of grip members 74 that extend out, for instance proximally, from the plate 72. The grip members 74 can be spaced such that the needle handle body 73 defines a bridge portion 76 connected between the grip members 74. The handle 70 defines an aperture 78 that extends longitudinally through the needle handle body 73, for instance through the bridge portion 76. At least a portion up to all of the aperture 78 is sized so as to retain the needle shaft 62. In accordance with the illustrated embodiment, the needle handle 70 is overmolded onto the proximal end 66 of the needle shaft 62. It should be appreciated that the needle handle body 73 can be discreetly connected to the needle shaft 62 or can be integral with the needle shaft 62 in accordance with any suitable embodiment as desired. In accordance with one embodiment, the needle handle 70 can include an attachment member such as a lure fitting 71 that facilitates attachment of the receptacle 45 to the needle 44.

It should further be appreciated that the needle handle 70 can be constructed in accordance with any embodiment as desired. For instance, referring to FIGS. 3D-F, the handle body 73 extends along a transverse length defined by a pair of opposed outer ends 73a and a middle portion 73b connected between the outer ends 73a. The handle body 73 can be bowed such that the outer ends 73a are disposed distal with respect to the middle portion 73b. The handle body 73 further defines a proximal end 74 and a distal end 76, whereby the proximal end 74 is bowed more than the distal end 76. For instance, the distal end 76 can be bowed or can extend substantially straight. The handle body 73 can be round along a central needle handle axis 69 that extends along the transverse length. The needle handle 70 can further define one or more slots 95 that extend into or through the handle body 73, so as to define an ergonomically friendly gripping region.

As described above with reference to FIGS. 3A-C, the handle 70 defines an aperture 78 that extends through the handle body 73 and is configured to retain the proximal end 66 of the needle shaft 62. For instance, as illustrated in FIGS. 3D-F, the aperture 78 can include a proximal portion 78a and a distal portion 78b that is disposed distal with respect to the proximal portion 78a. The distal portion 78b can be sized so as to retain the proximal end 66 of the needle shaft 62. For instance, the handle body 73 can be overmolded onto the proximal end 66 of the needle shaft 62. Alternatively, the handle body 73 can retain at least one fastener, such as a pair of pins 79 that can extend through the distal portion 78b of the aperture 78 and through the proximal end 66 of the needle shaft 62 so as to secure the needle handle 73 to the needle shaft 62. Thus, the distal portion 78b can be sized differently than the needle shaft 62. For instance, the distal portion 78b can be substantially hexagonal in shape, or can define any suitable geometry as desired. The proximal portion 78a can likewise define any suitable size and shape as desired. For instance, in accordance with the illustrated embodiment, the proximal portion 78a can be round, such as substantially cylindrical, and can define a beveled lead-in 78c at the proximal end of the proximal portion 78a. As described in more detail below, the handle 70 is configured to retain the receptacle 45 in the aperture 78, and thus can define an attachment member that is configured to attach the receptacle 45 to the needle 44.

The longitudinal axis 64 of the needle shaft 62 can be coincident with the longitudinal axis 48 of the trocar 42 when the needle 44 is operatively coupled to the trocar 42, such that at least a portion of the needle shaft 62 is slidingly received in the cannulation 47.

Figure 5A:
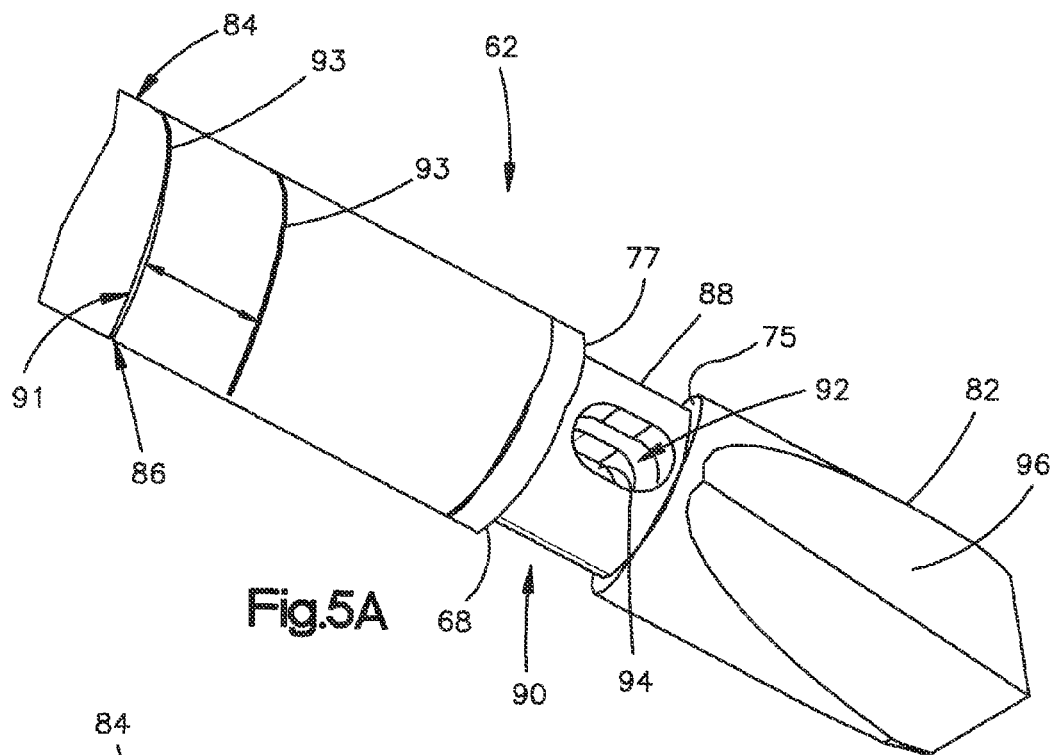
FIG. 5A is an enlarged perspective view of a portion of the distal end of the bone marrow harvesting needle illustrated in FIG. 2A.
Figure 5B:
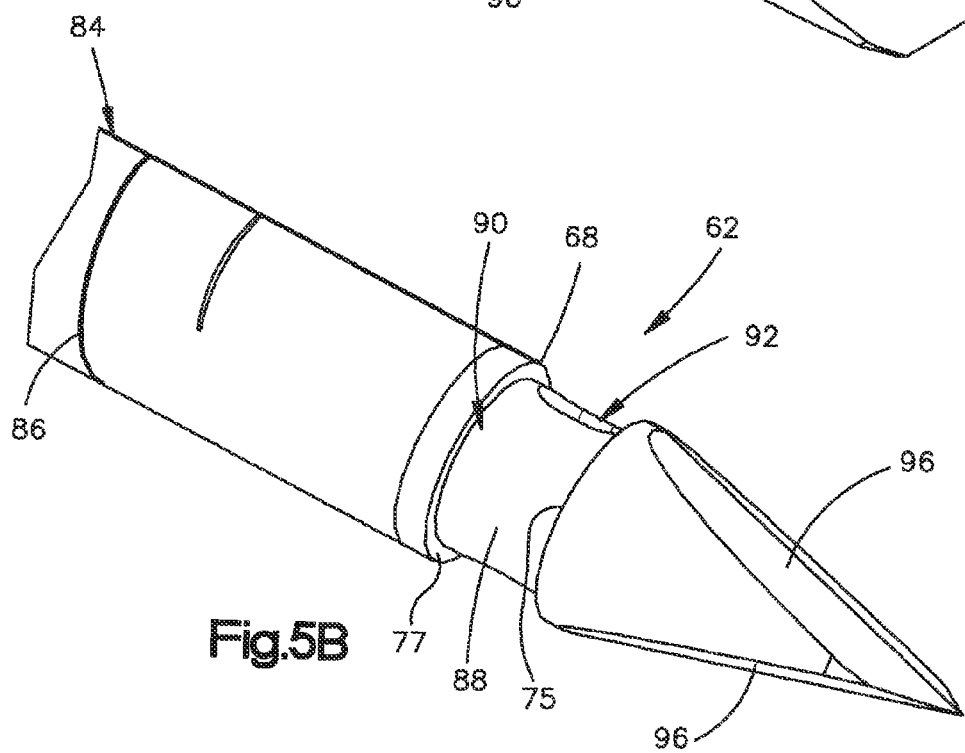
FIG. 5B is another enlarged perspective view of a portion of the distal end of the bone marrow harvesting needle illustrated in FIG. 5A.

As shown in FIGS. 5A-B, the needle 44 includes a tip 82 that extends distally from the needle shaft 62. In accordance with one embodiment, the needle shaft 62 defines a neck 88 that extends distally from the shaft body 63, and extends distally from the flexible portion 84 in accordance with the illustrated embodiment. For instance, the neck 88 can extend from the distal end 68 of the shaft body 63. The neck 88 can be recessed along a radial direction that is transverse with respect to the central axis 64 of the needle shaft 62. It should be appreciated that the neck 88 can be spaced from the flexible portion any distance as desired, such as approximately 0.0787 inch in accordance with the illustrated embodiment, it can nevertheless be said that the next 88 extends distally from the flexible portion 84.

The tip 82 can extend distally from the neck 88 and also therefore extends distally with respect to shaft 62. For instance, the tip 82 extends distally with respect to the flexible portion 84. Thus, the flexible portion 84 can be disposed distal with respect to the rigid portion 81 and proximal with respect to the tip 82. Alternatively, the shaft 62 can be devoid of the neck 88, such that the tip 82 extends directly from the flexible portion 84. Alternatively still, the shaft body 63 can include a rigid portion disposed distal of the flexible portion 84. It should be further appreciated that the shaft body 63 can be devoid of a rigid portion, such that a substantially entirety of the shaft body 63 is flexible.

The neck 88 can be connected between the shaft body 63 and the tip 82, for instance between the flexible portion 84 and the tip 82. While the flexible portion 84 terminates at a location proximal of the neck 88, it should be appreciated that the neck 88 can alternatively extend radially into the flexible portion 84. Furthermore, the needle shaft 62 can define more than one neck 88 positioned as desired. Thus, it can be said that the needle 44, and in particular the needle shaft 62, defines at least one neck 88. The neck 88 can be recessed with respect to the shaft body 63 so as to define a first or proximal shoulder 77 that extends substantially radially between the shaft body 63 and the neck 88 and a second or distal shoulder 75 that is opposite the proximal shoulder 77 and extends substantially radially between the tip 82 and the neck 88. The neck 88 can define a pocket 90 that can be radially undercut at a location longitudinally between the opposed shoulders 75 and 77, respectively, and thus between the shaft body 63 and the 82. In particular, the pocket 90 is radially recessed with respect to the flexible portion 84 such that the neck 88 defines an outer cross-sectional dimension that is less than that of at least a portion, such as a portion that is adjacent the neck 88, of the shaft body 63. The pocket 90 can further be radially recessed with respect to the largest cross-sectional dimension of the tip 82. While the pocket 90 extends around the entire perimeter of the neck 88, the pocket 90 can alternatively extend about only a portion of the perimeter. Alternatively, the needle shaft 62 can define a plurality of pockets 90 that are spaced about the neck 88. As described in more detail below, the needle 44 defines at least one bone marrow aspirate intake port 92 such as a pair of bone marrow aspirate intake ports 92 that extend radially into the needle shaft 62, for instance at the pocket 90.

The needle 44 defines a cannulation 80 that extends along the central axis 64 of the shaft body 63 from the proximal end 66 through the distal end 68 of the shaft body 63. However, the cannulation 80 does not extend through the needle shaft 62 in accordance with the illustrated embodiment, but rather terminates at a location radially aligned with the intake ports 92. The proximal end 66 of the shaft body 63 can be coupled to the receptacle 45 such that the receptacle 45 is in fluid communication with the cannulation 80 and thus configured to receive the aspirated bone marrow from the needle 44.

The shaft body 63 defines an outer diameter (or alternatively shaped cross-sectional dimension) that is substantially equal to, or slightly less than, that of the cannulation 47 of the trocar shaft 46, such that the needle shaft 62 can be slidably inserted into the cannulation 47 in the longitudinal direction when the flexible portion 84 is in the first unflexed configuration so as to operably couple the needle 44 to the trocar 42. Accordingly, the trocar 42 can support the needle 44 as the needle 44 is advanced into the cancellous portion of the target bone. In particular, the shaft body 63 has a longitudinal length greater than that of the trocar shaft 46, and the needle tip 82 can be inserted distally into the proximal end 49 of the trocar shaft 46, through the cannulation 47, and out the distal end 50 into the cancellous bone portion. In accordance with one embodiment, a first or distal length of the flexible portion 84 extends out from the trocar shaft 46, and a second or proximal length of the flexible portion 84 remains disposed within the cannulation 47 of the trocar shaft 46. For instance, the shaft body 63 can be configured such that at least approximately 0.2 inch of the flexible portion 84 can be disposed inside the cannulation 47 when the tip 82 protrudes approximately 3.35 inches out from the trocar shaft 46 along the central axis 64. While the needle shaft 62 and cannulation 47 are illustrated as substantially cylindrical in shape, it should be appreciated that they can define any suitable alternative shape as desired.

Referring also to FIGS. 4A-5A, the shaft body 63 defines a radially inner surface 65 that defines the perimeter of the cannulation 80 and an opposed radially outer surface 67. The inner surface 65 can define any suitable cross-sectional dimension, such as a diameter, as desired, for instance between approximately 0.05 inch and approximately 0.10 inch, including approximately 0.086 inch. The outer surface 67 can define any suitable cross-sectional dimension, such as a diameter, as desired, for instance between approximately 0.07 inch and approximately 0.15 inch, including approximately 0.01085 inch. As described above, at least a portion up to all of the shaft body 63 is flexible and can bend, for instance at the flexible portion 84, such that a corresponding portion of the central axis 64 transitions from extending along the longitudinal direction L to extending along a path that is offset with respect to the longitudinal direction L. For instance, the offset path can be curved. In accordance with the illustrated embodiment, the flexible portion 84 can be inserted into the cancellous bone portion of the target bone during operation of the bone marrow harvesting device 40. In accordance with the illustrated embodiment, the flexible portion 84 is defined by a groove 86 that extends substantially along a helical path 91 along a length of the shaft body 63, the length being at least a portion up to substantially all of the shaft body 63. The groove 86 can project radially (e.g., substantially perpendicular to the central axis 64) into the outer surface 67 and extends along the helical path 91 that is elongate along a helical direction of extension along the longitudinal length of the flexible portion 84. The groove 86 can terminate at the first or proximal shoulder 77, or can terminate at a location spaced from the first or proximal shoulder along the central axis 64 any distance as desired, for instance approximately 0.0787 inch.

In accordance with the illustrated embodiment, the helical path 91 can define a constant pitch along the longitudinal length of the flexible portion 84. Thus, adjacent revolutions 93 of the groove 86 can be spaced at a substantially constant longitudinal distance D along the length of the flexible portion 84, the length extending along the longitudinal direction L. Alternatively, adjacent revolutions of the groove 86 can be spaced at increasing or decreasing longitudinal distances in a distal direction along the length of the flexible portion 84. Furthermore, the path 91 can be helical as described above, or can define any suitably shaped path unless otherwise indicated.

The groove 86 can be defined a single continuous cut into the flexible portion 84 of the needle shaft 62, such that the flexible portion 84 is devoid of any additional cuts. Thus, the groove 86 can be a single continuous groove, meaning that the flexible portion 84 of the needle shaft 62 can be devoid of any other grooves constructed substantially identically to the groove 86. Thus, the flexible portion 84 of the needle shaft 62 includes the groove 86 and is devoid of more than one groove 86.

Furthermore, the groove 86 can define a straight line as illustrated (see FIGS. 5A-B), or can define any suitable alternative shape as desired, such as a serpentine path as illustrated. For instance, as illustrated in FIGS. 5C-D, the groove 86 can define a plurality of joints 130 that can define substantially dovetail-shaped joints including a plurality of tongues 132 and a plurality of recesses 134 that retain the tongues 132, such that the tongues 132 are movable in the recesses 134. In accordance with the illustrated embodiment, at least a portion up to an entirety of the tongues 132 flare outward along a direction into the respective recesses. For instance, each of the tongues 132 defines a neck 136 that extends into the corresponding recess 134, an end wall 138 opposite the neck and disposed in the corresponding recess 134, and a pair of opposed side walls 140 that are connected between the neck 136 and the end wall 138. The side walls 140 are spaced along a direction substantially parallel to the helical path 91, and can flare away from each other along a direction into the respective recess 134, such that the side walls 140 flare away from each other along a direction from the neck 136 to the end wall 138. The end walls 138 can extend along a direction substantially parallel to the helical path 91, such that line extending perpendicular to the helical path 91 can bisect the dovetail joints 130. Accordingly, when a torsional force is applied to the needle shaft 62, and thus the flexible portion 84, adjacent side walls 140 of adjacent joints 130 can cam against each other so as to provide a retention force that biases the respective tongues 132 into the corresponding recesses 134. Alternatively, referring to FIG. 5E, the side walls 140 of each joint 130 can extend substantially parallel to each other along a direction between the neck 138 and the end wall 138. The helical path 91 can define an angle θ with respect to a plane P that extends substantially perpendicular to the central axis 64. The angle θ can be as desired, such as between approximately 10.5 degrees and approximately 13.5 degrees, and for instance approximately 12 degrees.

In accordance with the illustrated embodiment, the side walls 140 are curved, and define radii of curvature at the interface with the end wall 138. For instance, the radius of curvature defined at the interface with the end wall 138 and each of the side walls 140 can be approximately 0.0054 inch, or any suitable alternative dimension as desired. The center of the radii can be spaced apart any suitable distance such as approximately 0.0285 inch. Adjacent end walls 138 can be spaced along a direction substantially perpendicular to the helical path any suitable distance as desired, such as approximately 0.021 inch. The joints 130 can define one or more curved surfaces at the interface between the end walls 138 and the side walls 140. For instance, the curved surfaces can be defined by any suitable radius as desired, such as approximately 0.0054 inch. The center of the radii of each joint can be spaced apart any distance as desired, such as approximately 0.0285 inch. Alternatively, the interface between the end walls 138 and the side walls 140 can define substantially straight and angled surfaces. It should be appreciated that the side walls 140 can alternatively extend substantially straight or include angled straight segments as desired.

In accordance with the illustrated embodiment, the groove 86 can define any suitable number of joints 130 along a revolution about the needle shaft 62 along the helical path. The groove can define greater than 4.5 and less than 20, for instance between approximately 4.8 and approximately 5.0 cycles per revolution 93 about the needle shaft 62. That is, the groove 86 can define approximately 5.0 segments S defined between the respective midpoints of adjacent end walls that are spaced along a direction substantially parallel to the helical path 91 along a single revolution 93 about the needle shaft 62. In accordance with an alternative embodiment, the groove 86 can define approximately 12.0 cycles per revolution about the needle shaft 62. The flexible portion 84, and the rigid portion 81 can define any suitable outer cross sectional dimension, such as a diameter, of approximately 0.1085 inch as described above, and any suitable inner cross-sectional dimension, such as a diameter, of approximately 0.085 inch as described above. Furthermore, the helical path 91 can define any suitable pitch as desired, such as a distance of approximately 0.0762 inch that extends along a direction substantially parallel to the central axis 46 between adjacent revolutions 93. The dovetail joints 61 can define a height, for instance the distance between the neck 136 and the corresponding end wall 138 as desired, for instance approximately 021 inches.

When the central axis 64 extends along the longitudinal direction L, for instance when the flexible portion 84 is in the unflexed configuration, the groove 86 can define any suitable thickness as desired, such as between approximately 0.005 inch and approximately 0.02 inch, for instance approximately 0.01 inch. The thickness is substantially perpendicular to the helical path along the length of the shaft body that defines the helical path 91. The tongues 132 are movable in the recesses 134 along a direction that includes a directional component that is parallel to the central axis 64. Thus, the flexible portion 84 can be bent in the manner described above such that at one side of the flexible portion 84, the joints 130 are placed in compression such that the respective tongues 132 are moved further into the corresponding recesses 134 so as to decrease the thickness of the groove 86, while simultaneously at a radially opposite side of the flexible portion 84, the joints 130 are placed in tension such that the respective tongues 132 are moved further out of the corresponding recesses 134 so as to increase the thickness of the groove 86.

Thus, the helical groove 86 allows the flexible portion 84 of the needle shaft 62 to flex or bend relative to the longitudinal direction L. As a result, the shaft body 63, and thus the needle shaft 62, can move from a straight configuration as illustrated in FIG. 4A whereby the needle shaft 62, including the flexible portion 84, extends along the central axis 64 which extends along the longitudinal direction L, to a flexed configuration as illustrated in FIG. 4B whereby the flexible portion 84, and thus the central axis 64, is flexed and curved relative to the longitudinal direction L. In accordance with one embodiment, the flexible portion 84 can be configured to flex to any angle as desired with respect to the longitudinal direction L. For instance, the flexible portion 84 is configured to flex so as to define an angle between approximately 45 degrees and approximately 90 degrees with respect to the longitudinal direction L, including between approximately 85 degrees and approximately 90 degrees. While the flexible portion 84 is illustrated as including the grooves 86 that extend into or through the shaft body 63, the flexible portion 84 can additionally or alternatively be configured as a flexible material that extends distally from the shaft body 63. For instance, the flexible portion 84 can be made from polyetheretherketone (PEEK) or any suitable alternatively flexible material, and can include grooves 86 or can be devoid of grooves 86.

Referring now to FIG. 4C, in accordance one embodiment, the groove 86 extends radially inwardly into the outer surface 67, but does not extend through the shaft body 63 to the inner surface 65. Thus, as illustrated in FIG. 4C, the groove 86 has a depth that terminates at a location between the inner and outer surfaces 65 and 67. The depth can sufficient to impart flexibility onto the shaft body 63. As a result, the inner surface 65 can be substantially smooth. Alternatively, as illustrated in FIG. 4D, the groove 86 can extend radially through the needle shaft 62, from the outer surface 67 and through the inner surface 65 to increase the flexibility of the shaft body 63 at the flexible portion 84. In accordance with one embodiment, the groove 86 can be laser-cut into the shaft body 63, though it should be appreciated that the groove 86 can be formed in any suitable alternative manner as desired.

The needle 44 can include a polymeric sheath or overcoat 85 that covers at least some of the flexible portion 84 of the needle shaft 62, such as all of the flexible portion 84. The polymeric overcoat 85 can seal the flexible portion 84, can protect the integrity of the needle shaft 62, and can provide stability that decreases the flexibility of the flexible portion 84 as desired. The needle 44 can include the polymeric overcoat 85 whether the groove 86 extends into but not through the flexible portion 84 as illustrated in FIG. 4C, or whether the groove 86 extends through the flexible portion through to the cannulation 80. The overcoat 85 can be non-elastomeric and, for instance, can be made from PEEK or any suitable alternative non-elastomeric material. Furthermore, the overcoat 85 can extend over the groove 86 without extending into the groove 86.

Referring to FIGS. 5A-B, and as described above, the distal end 68 of the needle shaft 62 is connected to the needle tip 82. The needle tip 82 is configured to advance through the cancellous portion of the target bone as desired to a depth such that the flexible portion 84 is also inserted into the cancellous bone portion. The needle tip 82 can be tapered, and is illustrated as a chisel tip having opposed surfaces 96 that taper toward each other as they extend distally with respect to the neck 88 and the flexible portion 84. Alternatively, the tip 82 can be configured as a spiral-shaped drill-bit, a bullnose, a sharp or blunted cone, a hemisphere, a spade, or any alternative shape as desired. For instance, referring to FIGS. 8A-B, the tip 82 can define a recess 97 so as to be configured as a self-tapping top that includes at least one or more radially projecting cutting flutes 99 that can be curved or shaped as desired about the central axis 64 as they extend longitudinally.

Figure 8A:
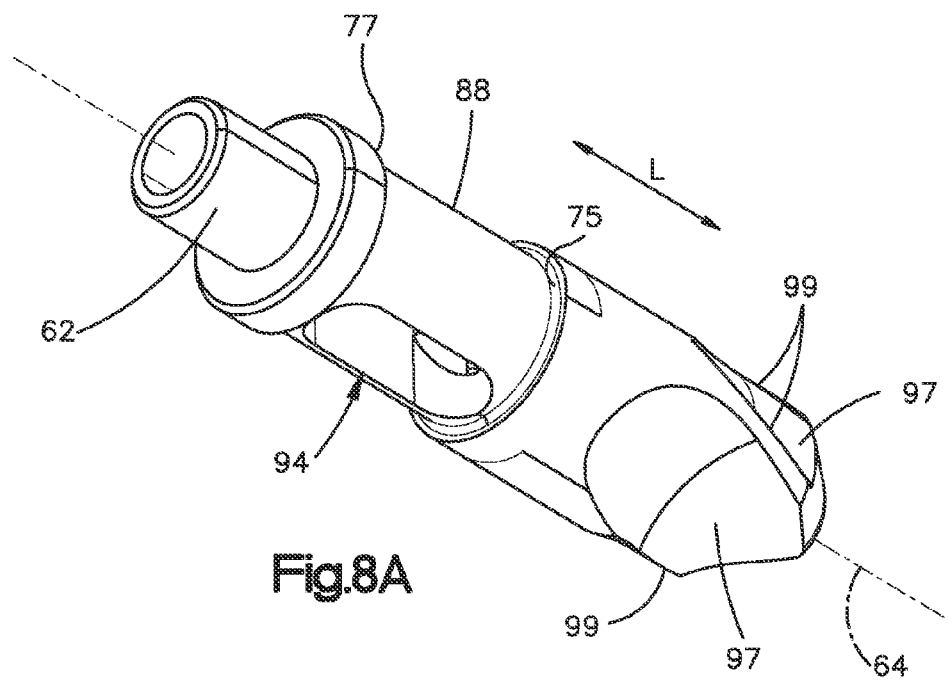
FIG. 8A is a perspective view of a cutting tip of the needle illustrated in FIG. 2A, but constructed in accordance with another embodiment.
Figure 8B:
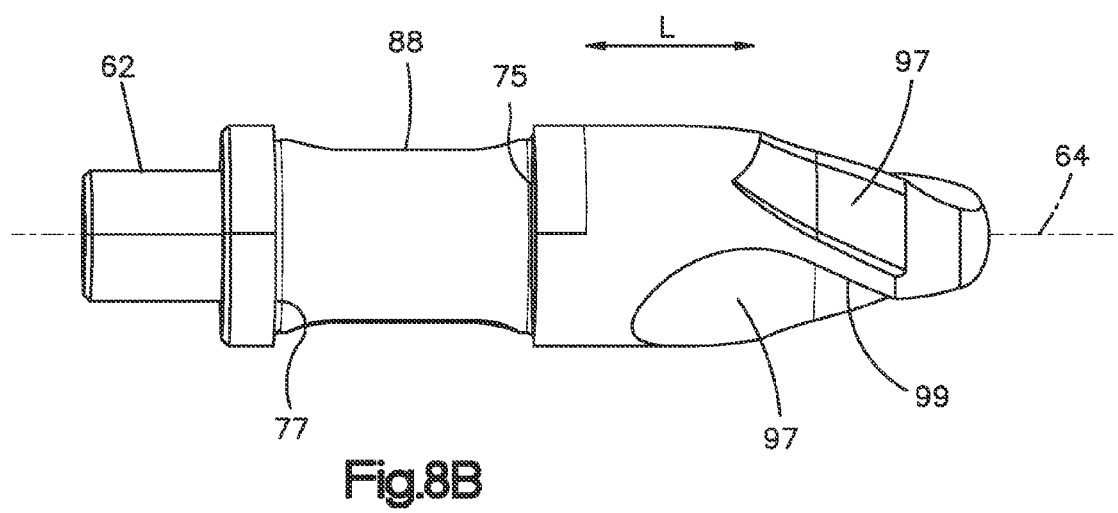
FIG. 8B is a side elevation view of the cutting tip illustrated in FIG. 8A.

As illustrated in FIGS. 8A-B, the neck 88 can define a cross-sectional dimension along a direction perpendicular to the central axis 64 that is less than the cross sectional dimension of the needle shaft 62 along a direction perpendicular to the central axis 64, and thus also less than the cross-sectional dimension of the flexible portion 84 along a direction perpendicular to the central axis 64, as desired. The tip 82 can define any distance from the neck 88 as desired. In accordance with one embodiment, the proximal end of the tip 82 is disposed any distance as desired from the distal end of the cannulation 80, such as between approximately 0.05 mm and 1.5 mm, including approximately 0.07874 mm. Thus, the tip 82 can be configured to be advance through the cancellous portion of the target bone, for instance by applying a biasing force to the needle 44 in the longitudinal direction L, for instance by punching the needle 44, so as to drive the needle tip 82 along the cancellous portion of the target bone, or by applying a torsional force to the needle that causes the needle tip 82 to rotate about an axis of rotation that can be defined by the central axis 64 so as to drive the needle tip 82 along cancellous portion of the target bone. Alternatively still, it should be appreciated that if the bone marrow harvesting device 40 is devoid of the stylet 150 described above, the needle tip 82 can be configured to be driven through the cortical wall of the target bone, for instance by applying the driving force to the needle handle 70 once the needle tip 82 has been placed against the cortical wall.

With continuing reference to FIGS. 5A-B, the cannulation 80 of the shaft body 63 is in communication with the ambient environment of the needle 44. In particular, as described above, the needle 44 defines at least one transverse aspirate intake port 92 illustrated as an aperture 94 that extends radially into the needle shaft 62 along a direction that is substantially perpendicular or otherwise angularly offset with respect to the central axis 62 of the needle shaft 62. For instance, in accordance with the illustrated embodiment, the intake port 92 extends radially into the neck 88. It should be appreciated, however, that the intake port can extend through any suitable location of the needle 44 in communication with the cannulation 80 and sufficient to receive aspirated bone marrow from the target bone. For instance, in accordance with an alternative embodiment, the intake port 92 can extend into the tip assembly 87, such as the tip 82.

The aperture 94 extends into the needle shaft 62 to a depth such that the aperture 94 intersects the cannulation 80 and thus places the intake port 92 in fluid communication with the cannulation 80. In accordance with the illustrated embodiment, the aperture 94 extends through the neck 88 so as to define a pair of opposed, for instance radially opposed, intake ports 92 that can be radially opposed, and in communication with the cannulation 80. The intake ports 92 can define any area as desired, for instance greater than approximately 0.005 in2, such as greater than approximately 0.006 in2, and less than any value as desired, such as 0.023 in2. While the intake ports 92 are illustrated as angularly offset with respect to the cannulation 80, the cannulation 80 can be configured to extend longitudinally through the tip 82 so as to be placed in communication with the ambient environment, such that the intake port 92 is coextensive with the cannulation 80. Thus, the needle shaft 62 defines an aspiration channel 83 that extends through the needle body 63, and can include the cannulation 80 and the intake port 92.

As described above with respect to FIGS. 2A-D, and with further reference to FIGS. 6A-B, the trocar 42 can create an opening through the cortex 98 of a target bone 100, which can be any bone having a desired amount of bone marrow to be aspirated. For instance, the target bone 100 can be an iliac crest, a long bone, a vertebral body, or any alternative suitable bone as desired. Referring also to FIGS. 6A-B, the needle tip 82 can be inserted through the cannulation 47 of the trocar 42 and into the cancellous portion 102 of the target bone 100. The tip 82 can be advanced in the bone 100 as a negative pressure is induced that draws bone marrow aspirate from the cancellous portion 102 along the direction of Arrow 103. The tip 82 can be positioned such that the intake ports 92 are aligned with bone marrow 105, such that the induced negative pressure draws the bone marrow into the receptacle 45 as bone marrow aspirate. Conventional needles 20 of the type illustrated in FIG. 1, while suitable for facilitating the removal of bone marrow aspirate from the cancellous portion of bone, are not flexible and thus can cause damage to the cortical wall if it encounters an anatomical curvature of the bone, and in some instances can punch through the cortex 98. Accordingly, clinicians typically withdraw large volumes from a single location in the cancellous portion without repositioning the needle, which typically causes the aspirated bone marrow to be diluted by a significant amount of peripheral blood that is also aspirated.

Referring to FIGS. 6A-B, the needle 44 has sufficient strength to advance through the cancellous portion 102 of the target bone 100 while allowing the flexible portion 84 to flex to the contour of an anatomical curvature 103 of the bone 100. Accordingly, the tip 82 is configured to advance in the cancellous portion 102 without punching into or through the internal surface of the cortex 98. Accordingly, the tip 82 can be driven further into the cancellous portion 102 as compared to conventional needles, and can reach bone marrow that was previously unattainable due to the curvature of, for instance, the iliac crest. As a result, the needle 44 is capable of drawing a higher proportion of bone marrow aspirate with respect to peripheral blood than conventional needles. Furthermore, the intake ports 92 are recessed with respect to the shoulders 75 and 77 of the tip 82 and the needle body 63, thereby reducing the instances that the intake ports 92 will be fouled by bone fragments or other debris disposed within the cancellous portion 102.

Referring again to FIG. 2A, the receptacle 45 can be provided as a syringe 104 that includes a barrel 106 that defines an interior void 108 that is in fluid communication with the aspiration channel 83 when the receptacle 45 is coupled to the needle 44. The barrel 106 has a tip 110 at one end that is configured to be placed in fluid communication with the needle 44, and is closed by a plunger 112 at an opposite end. The tip 110 can be configured to operably couple the syringe 104 to the needle 44 such that the interior void 108 is in fluid communication with the cannulation 80. Accordingly, the plunger 112, which is movably coupled to the barrel 106, can be manually drawn proximally with respect to the barrel 106 so as to induce a negative pressure in the aspiration channel 83 that causes bone marrow to be drawn through the aspiration channel 83 and into the interior void 108. In accordance with the illustrated embodiment, the bone marrow aspirate is drawn through the intake ports 92, into the cannulation, and travels proximally into the interior void 108.

Figure 7A:
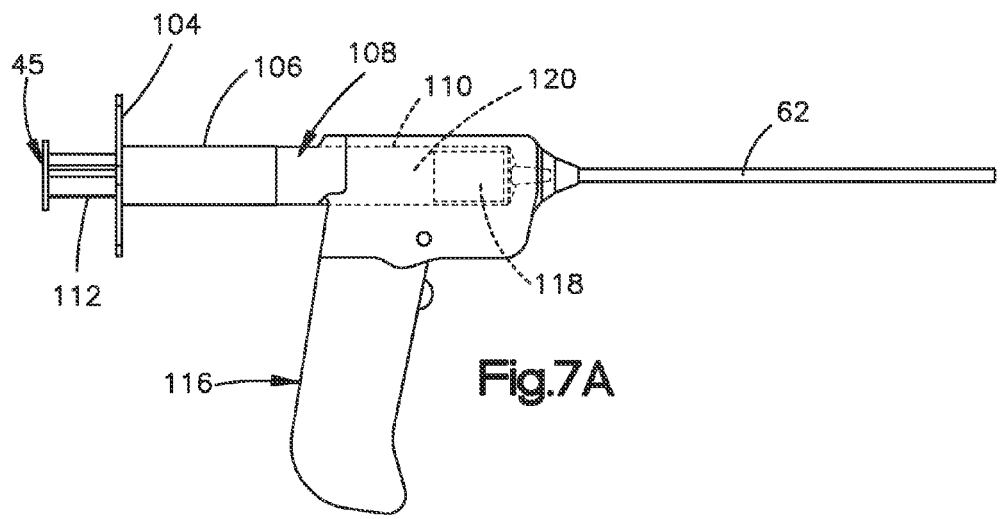
FIG. 7A is a side elevation view of a receptacle constructed in accordance with an alternative embodiment, shown coupled to the bone marrow harvesting needle illustrated in FIG. 2A.
Figure 7B:
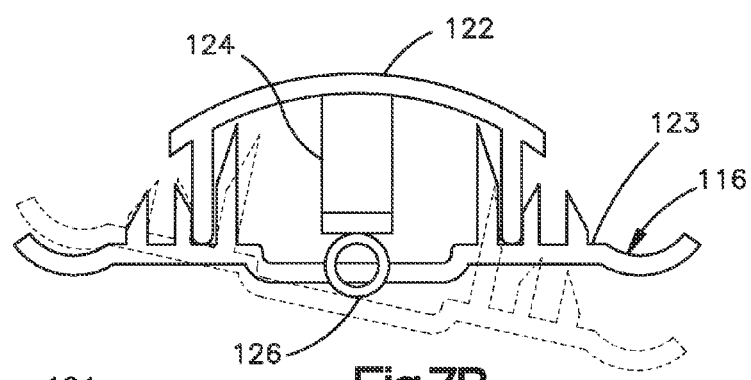
FIG. 7B is an end elevation view of a choke actuator of the receptacle illustrated in FIG. 7A.
Figure 7C:
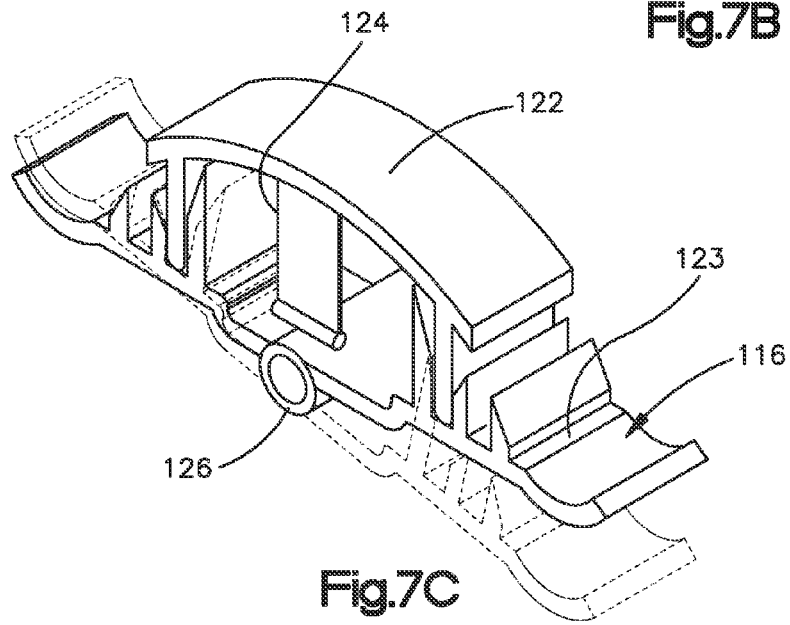
FIG. 7C is a perspective view of the choke actuator of the receptacle illustrated in FIG. 7B.

Alternatively, referring to FIGS. 7A-C, the receptacle can be coupled to an aspirator tool 116 having a motor 118, a syringe 104, and a conduit 120 that couples the motor 118 to the syringe 104. The motor 118 can be a stepper motor that induces a vacuum in the aspiration channel 83 in the manner described above, which causes the bone marrow aspirate to travel through the conduit 120 and into the barrel 106. The aspirator tool 116 can include an actuator in the form of a pushbutton 122 and an opposed brace 123 that carries the conduit 120. The pushbutton 122 is coupled to a crimp member 124 configured to be driven down onto the conduit 120 when the pushbutton 122 is depressed, thereby blocking the channel between the needle 44 and the receptacle 45, and restricting or preventing the flow of aspirate through the conduit 120 into the barrel 106. For instance, the pushbutton 122 can be depressed to block aspiration as the tip 82 is being repositioned in the target bone.

It should be noted that the illustrations and discussions of the embodiments shown in the figures are for exemplary purposes only, and should not be construed limiting the disclosure. One skilled in the art will appreciate that the present disclosure contemplates various embodiments. It should be further appreciated that the features and structures described and illustrated in accordance one embodiment can apply to all embodiments as described herein, unless otherwise indicated. Additionally, it should be understood that the concepts described above with the above-described embodiments may be employed alone or in combination with any of the other embodiments described above.

What is claimed:

1. A bone marrow harvesting device comprising:
 a bone marrow needle including:
  a needle shaft that is elongate along a central axis, the needle shaft including a shaft body, the needle shaft defining an aspiration channel that extends through the shaft body along the central axis, wherein the shaft body includes a flexible portion defining a single continuous groove that extends into the shaft body, the single groove extending along a substantially helical path along a length of the shaft body, and the needle shaft defines a neck that is recessed with respect to the flexible portion and the neck that is recessed defining an intake port in fluid communication with the aspiration channel, such that the intake port extends through the recessed neck;
  a tip that extends distally from the needle shaft; and
  a non-elastomeric overcoat that extends over the flexible portion and covers at least a portion of the groove; and
 a trocar including a trocar handle and a cannulated trocar shaft that extends from the trocar handle, the cannulated shaft configured to slidingly receive at least a portion of the needle shaft.

2. The bone marrow harvesting device as recited in claim 1, wherein the groove extends through the shaft body into the aspiration channel.

3. The bone marrow harvesting device as recited in claim 1, wherein the flexible portion comprises a flexible material.

4. The bone marrow harvesting device as recited in claim 1, wherein the neck is disposed between the flexible portion and the tip.

5. The bone marrow harvesting device as recited in claim 1, wherein the nonelastomeric overcoat does not extend into the groove.

6. The bone marrow harvesting device as recited in claim 5, wherein the nonelastomeric overcoat is made from PEEK.

7. The bone marrow harvesting device as recited in claim 1, wherein the groove is substantially straight.

8. The bone marrow harvesting device as recited in claim 7, wherein the groove defines a serpentine shape.

9. The bone marrow harvesting device as recited in claim 8, wherein the groove defines a joint including a plurality of tongues and corresponding recesses that retain the tongues, such that the tongues are movable in the recesses along a direction that includes a directional component that is parallel to the central axis.

10. The bone marrow harvesting device as recited in claim 9, wherein the joint substantially defines a dovetail shape, such that at least a portion of the tongues flare outward along a direction into the respective recesses.

11. The bone marrow harvesting device as recited in claim 10, wherein the flexible portion defines greater than 4.5 and less than 20 dovetail joints per revolution about the needle shaft.

12. The bone marrow harvesting device as recited in claim 11, wherein the flexible portion defines between approximately 4.8 and approximately 5.0 dovetail joints along a single revolution about the needle shaft.

13. The bone marrow harvesting device as recited in claim 9, wherein the groove defines a thickness between approximately 0.005 inch and approximately 0.02 inch, the thickness substantially transverse to the helical path along the length of the shaft body.

14. The bone marrow harvesting device as recited in claim 13, wherein the thickness is approximately 0.01 inch.

15. The bone marrow harvesting device as recited in claim 13, wherein the helical path defines an angle between approximately 10.5 degrees and approximately 13.5 degrees with respect to a plane that extends substantially perpendicular to the central axis.

16. The bone marrow harvesting device as recited in claim 9, wherein the tongue defines opposed side walls that are spaced along a direction substantially parallel to the helical path, and the opposed side walls extend substantially parallel to each other.

17. The bone marrow harvesting device as recited in claim 15, wherein the angle is approximately 12 degrees with respect to the plane.

18. The bone marrow harvesting device as recited in claim 1, wherein the bone marrow needle further includes a needle handle coupled to the needle shaft.

19. The bone marrow harvesting device as recited in claim 1, further comprising a stylet that includes a stylet handle, a stylet shaft that extends from the stylet handle, and a stylet tip that extends from the stylet shaft, wherein the stylet tip is configured to be driven through a cortical wall of the target bone.

20. The bone marrow harvesting device as recited in claim 19, wherein the stylet shaft is sized to extend through the cannulated trocar shaft such that the stylet tip projects outward with respect to the trocar shaft.

21. The bone marrow harvesting device as recited in claim 1, wherein approximately 0.2 inch of the flexible portion can be disposed inside the cannulated trocar shaft when the tip protrudes approximately 3.35 inches out from the trocar shaft along the central axis.

22. The bone marrow harvesting device as recited in claim 1, wherein the cannulated trocar shaft defines a proximal end and a distal end that is spaced from the proximal end along a central axis that extends along a longitudinal direction, and the flexible portion of the shaft body is configured to flex so as to define an angle between approximately 45 degrees and approximately 90 degrees with respect to the longitudinal direction L.

23. The bone marrow harvesting device as recited in claim 22, wherein the angle is between approximately 85 degrees and approximately 90 degrees.

24. The bone marrow harvesting device as recited in claim 1, further comprising a receptacle configured to be operatively coupled to the needle so as to aspirate bone marrow from a target bone through the needle and collect the aspirated bone marrow.

25. The bone marrow harvesting device as recited in claim 24, wherein the receptacle includes a barrel that defines an interior void in fluid communication with the channel, and a plunger movable attached to the barrel, such that movement of the plunger induces a negative pressure in the channel.

* * * * *